US012228860B2

(12) United States Patent
Sasao et al.

(10) Patent No.: US 12,228,860 B2
(45) Date of Patent: Feb. 18, 2025

(54) COMPOUND, POLYMER, PATTERN FORMING MATERIAL, PATTERN FORMING METHOD, AND METHOD OF MANUFACTURING SEMICONDUCTOR DEVICE

(71) Applicant: Kioxia Corporation, Tokyo (JP)

(72) Inventors: Norikatsu Sasao, Kawasaki Kanagawa (JP); Koji Asakawa, Kawasaki Kanagawa (JP); Shinobu Sugimura, Yokohama Kanagawa (JP)

(73) Assignee: Kioxia Corporation, Tokyo (JP)

( * ) Notice: Subject to any disclaimer, the term of this patent is extended or adjusted under 35 U.S.C. 154(b) by 0 days.

(21) Appl. No.: 18/466,668

(22) Filed: Sep. 13, 2023

(65) Prior Publication Data

US 2024/0004298 A1 Jan. 4, 2024

Related U.S. Application Data

(63) Continuation of application No. 17/196,988, filed on Mar. 9, 2021, now Pat. No. 11,796,915.

(30) Foreign Application Priority Data

Sep. 18, 2020 (JP) ................................ 2020-157383

(51) Int. Cl.

*C07C 69/78* (2006.01)
*C08F 12/22* (2006.01)
(Continued)

(52) U.S. Cl.

CPC ................ *G03F 7/11* (2013.01); *C07C 69/78* (2013.01); *C08F 12/22* (2013.01);
(Continued)

(58) Field of Classification Search

CPC ........... G03F 7/11; C07C 69/78; C07C 69/76; C08F 12/22; H01L 21/0271; C09D 125/18
See application file for complete search history.

(56) References Cited

U.S. PATENT DOCUMENTS 5,314,931 A 5/1994 Yamada et al.
5,688,628 A 11/1997 Oie et al.
(Continued)

FOREIGN PATENT DOCUMENTS

CN 110407803 A 11/2019
JP S49-58190 A 6/1974
(Continued)

OTHER PUBLICATIONS

Yiding Xu et al., "Effects of Mesogenic Shape and Flexibility on the Phase Structures of Mesogen-Jacketed Liquid Crystalline Polymers with Bent Side Groups Containing 1,3,4-Oxadiazole," Macromolecules, vol. 42, pp. 2542-2550 (2009).
(Continued)

*Primary Examiner* — Sean M DeGuire
*Assistant Examiner* — Alexander N. Lee
(74) *Attorney, Agent, or Firm* — Finnegan, Henderson, Farabow, Garrett & Dunner, LLP

(57) ABSTRACT

A pattern forming material used for forming an organic film on a film to be processed of a substrate having the film to be processed, the organic film being patterned and then impregnated with a metallic compound to form a composite film which is used as a mask pattern when processing the film to be processed, the pattern forming material contains a polymer including a monomer unit represented by the following general formula (3),
(Continued)

(3)

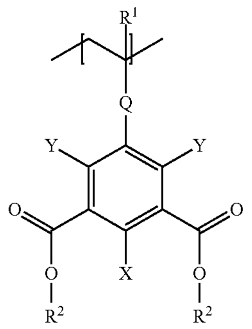

where, $R^1$ is H or $CH_3$, $R^2$ is a $C_{2-14}$ hydrocarbon group, Q is a $C_{1-20}$ hydrocarbon group, or an organic group containing an oxygen atom, a nitrogen atom, or a sulfur atom between carbon-carbon atoms or at a bond terminal of a $C_{1-20}$ hydrocarbon group, and X and Y are independently a hydrogen atom or a $C_{1-4}$ hydrocarbon group, at least one of them being the $C_{1-4}$ hydrocarbon group.

4 Claims, 2 Drawing Sheets

(51) Int. Cl.

| | |
|---|---|
| ***G03F 7/11*** | (2006.01) |
| ***H01L 21/027*** | (2006.01) |
| ***H01L 21/311*** | (2006.01) |
| *H10B 41/27* | (2023.01) |
| *H10B 43/27* | (2023.01) |

(52) U.S. Cl.

CPC .... *H01L 21/0271* (2013.01); *H01L 21/31116* (2013.01); *H01L 21/31144* (2013.01); *H10B 41/27* (2023.02); *H10B 43/27* (2023.02)

(56) References Cited

U.S. PATENT DOCUMENTS

| | | | |
|---|---|---|---|
| 7,026,406 | B1 | 4/2006 | Kawabe et al. |
| 9,487,600 | B2 | 11/2016 | Darling et al. |
| 9,768,059 | B1 | 9/2017 | Liu et al. |
| 2008/0188485 | A1 | 8/2008 | Baroudy et al. |
| 2014/0004464 | A1 | 1/2014 | Christianson et al. |
| 2014/0065546 | A1 | 3/2014 | Hatakeyama et al. |
| 2018/0173109 | A1 | 6/2018 | Gronheid et al. |

FOREIGN PATENT DOCUMENTS

| | | | |
|---|---|---|---|
| JP | 2001-310331 | A | 11/2001 |
| WO | WO 2013/165806 | A1 | 11/2013 |
| WO | WO 2018/135456 | A1 | 7/2018 |

OTHER PUBLICATIONS

Am. Chem. Soc., STN Registry Nos. 17469-29-5, 154719-02-5, 1438383-20-0, 1438262-80-6, 1425943-21-0, 1425942-94-4, 1416979-65-1, 1416979-63-9, 1299479-93-8, 1220869-25-9, 495338-46-0, 306297-06-3, 203855-94-1, 203855-87-2, 7 pages (2023).

Soutick Nandi a, Helge Reinsch b, Shyam Biswas, "A vinyl functionalized mixed linker CAU-10 metal-organic framework acting as a fluorescent sensor for the selective detection of H2S and palladium(II)", Microporous and Mesoporous Materials, Oct. 2019 (Year: 2019).

Zheng, Jun-Feng; Yu, Kai-Ling; Jiang, Xu-Qiang; Tang, Tao; Sun, Jia; Ding, Lin-Lin; Zhang, Rui; Zhao, Yang; Ren, Xiang-Kui; Xu, Jia-Ru; et al., "Side-Chain Jacketed Liquid Crystalline Polymer Forming Double-Chain Supramolecular Column and Hexagonal", Macromolecules 2018, 51, 6949-6957 (Year: 2018).

Jeny Karablinea and Moshe Portnoy, "Solid=phase synthesis and acidolytic degradation of sterically congested oliogoether dendrons" Org. Biomol. Chem., 2012,10, 4788-4794 (Year: 2012).

COMPOUND, POLYMER, PATTERN FORMING MATERIAL, PATTERN FORMING METHOD, AND METHOD OF MANUFACTURING SEMICONDUCTOR DEVICE

CROSS REFERENCE TO RELATED APPLICATION

This application is a continuation of U.S. patent application Ser. No. 17/196,988, filed Mar. 9, 2021, which is based upon and claims the benefit of priority from Japanese Patent Application No. 2020-157383, filed on Sep. 18, 2020; the entire contents of which are incorporated herein by reference.

FIELD

Embodiments described herein relate generally to a compound, a polymer, a pattern forming material, a pattern forming method and a method of manufacturing a semiconductor device.

BACKGROUND

There are increasing demands for a technology of forming high aspect ratio patterns in a manufacturing process of a semiconductor devices. High etch resistance is demanded for a mask pattern used for such a process because the mask pattern is exposed to etch gas for a long time.

SUMMARY

An embodiment of the present invention provides a polymerizable compound capable of producing a polymer which is useful as a pattern forming material and the polymer which is obtained by using the compound. Further, an embodiment of the present invention provides a pattern forming material capable of producing a mask pattern formed of a metal-containing organic film with high etch resistance, a pattern forming method using the pattern forming material, and a method of manufacturing a semiconductor device.

An embodiment provides a compound represented by the following general formula (1) (hereinafter, mentioned as a compound (1)), and a polymer including a monomer unit selected from monomer units derived from the compound (1).

(1)

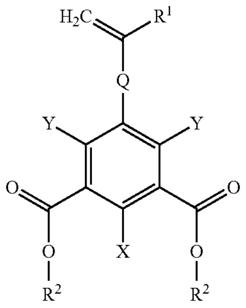

The embodiment further provides a compound represented by the following general formula (2) (hereinafter, mentioned as a compound (2)), and a polymer including a monomer unit selected from monomer units derived from the compound (2).

(2)

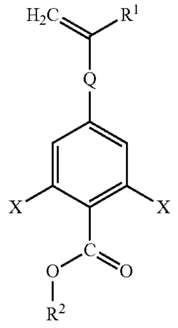

Note that, in the general formulas (1) and (2), $R^1$ is a hydrogen atom or a methyl group, $R^2$s are independently a $C_{2-14}$ hydrocarbon group in which α carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and X and Y are independently a hydrogen atom or a $C_{1-4}$ hydrocarbon group, at least one of X and Y being the $C_{1-4}$ hydrocarbon group.

The embodiment further provides a pattern forming material containing a polymer including a monomer unit selected from monomer units derived from the compounds (1) and (2), and a pattern forming method and a method of manufacturing a semiconductor device using the same.

DETAILED DESCRIPTION

Figure 1A:
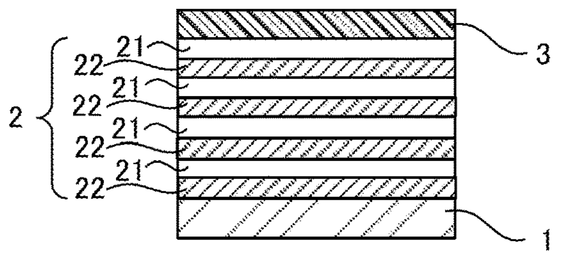
FIG. 1A is a view illustrating one process of a method of manufacturing a semiconductor device according to an embodiment.

Hereinafter, embodiments will be explained in detail with reference to the drawings Note that the present invention is not limited by the following embodiments. Further, components in the following embodiments include the ones easily assumed by those skilled in the art or substantially the same ones.

A polymer is a polymer formed by polymerization of monomers and is constituted of repeating units derived from the monomers. In this specification, the repeating unit constituting the polymer is referred to as a monomer unit. The monomer unit is a unit derived from a monomer, and a constituent monomer of the monomer unit means a monomer forming the monomer unit by the polymerization.

In this specification, a compound represented by a general formula (1) is also mentioned as a compound (1). Besides, a monomer unit represented by a general formula (3) is also mentioned as a monomer unit (3). Further, a monomer unit derived from the compound (1) is also denoted as a monomer unit (1). Similarly, a constituent monomer of the monomer unit (3) is denoted as a monomer (3). Also in a case of a compound and a monomer unit represented by another general formula or chemical structural formula, the compound and the monomer unit are sometimes similarly represented by symbols of the general formula or the chemical structural formula.

In consideration of the above problems, the present inventors have found a new polymerizable compound capable of producing a polymer which is useful as a pattern forming material. Further, the present inventors have found that a mask pattern with high etch resistance can be obtained by forming an organic film using the pattern forming material containing the polymer of the polymerizable compound having a specific substructure containing the compound, patterning the organic film, and then infiltrating the organic film with a metallic compound to form a composite film as the mask pattern. Infiltrating an organic film with a metallic compound is called "metallization". Concretely, the metallization can be performed by bonding a metallic compound to a portion of the organic film having a portion to which the metallic compound can be bonded. After bonding, the metallic compound may be subjected to, for example, a post-treatment such as oxidation. Hereinafter, a pattern forming material containing a specific polymer according to the embodiment of the present invention will be explained.

[Compound]

Examples of the compound of the embodiment are compounds represented by following the following general formulas (1) and (2).

(1)

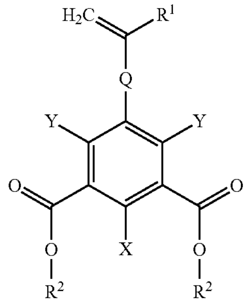

Note that in the above general formula (1), $R^1$ is a hydrogen atom or a methyl group, $R^2$ is a $C_{2-14}$ hydrocarbon group in which α carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and X and Y are independently a hydrogen atom or a $C_{1-4}$ hydrocarbon group, at least one of them being the $C_{1-4}$ hydrocarbon group.

(2)

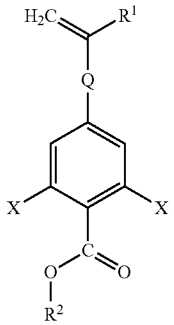

Note that in the above general formula (2), $R^1$ is a hydrogen atom or a methyl group, $R^2$ is a $C_{2-14}$ hydrocarbon group in which α carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and Xs are independently a hydrogen atom or a $C_{1-4}$ hydrocarbon group, at least one of them being the $C_{1-4}$ hydrocarbon group.

Note that in the case where there is one carbonyl group bonded to the benzene ring as in the above general formula (2), when X is a relatively large substituent, a later-explained composite film formed using a polymer derived from the compound is high in stability and excellent in etch resistance, so that the carbon number of X is preferably 2 to 4.

$R^2$ may be linear, branched, or cyclic, and is preferably, for example, an ethyl group, an n-propyl group, an isopropyl group, an n-butyl group, an isobutyl group, an s-butyl group, or a t-butyl group.

The hydrocarbon group of each of X and Y may be linear, branched, or cyclic, and is preferably, for example, a methyl group, an ethyl group, an n-propyl group, an isopropyl group, an n-butyl group, an isobutyl group, an s-butyl group, or a t-butyl group. At least one of X and Y only needs to be the hydrocarbon group, which means the combinations of one or more of Ys being hydrocarbon groups and X being a hydrogen atom, all Ys being hydrogen atoms and X being a hydrocarbon group, and one or more of Ys being hydrocarbon groups and X being a hydrocarbon group in the compound of the general formula (1), and means that one or more of Xs are hydrocarbon groups in the compound of the general formula (2).

When Q is the hydrocarbon group, it may be linear, branched, or cyclic, and may be an aliphatic group or an aromatic group. Having an aromatic ring is preferable in terms of etch resistance of an obtained composite film. The carbon number of the hydrocarbon group is preferably 1 to 10 when the hydrocarbon group does not have the ring, and preferably 6 to 18 when the hydrocarbon group has the ring. In the hydrocarbon group, the hydrogen atom may be substituted by a halogen atom, and examples of the halogen atom include F, Cl, Br.

Examples of the hydrocarbon group include a methylene group, an ethylene group, a propylene group, a butylene group, a 1,4-phenylene group, a 1,4-naphthalene group, a 1,4-anthracene group, and the like.

When Q is the organic group, it needs to be a group having a structure containing at least one of an oxygen atom, a nitrogen atom, or a sulfur atom between carbon-carbon atoms or at a bond terminal of the above hydrocarbon group. In other words, the organic group only needs to have an —O— bond, an —S— bond, or an —N— bond, and may form a bond such as an ester bond, a thioester bond, or an amide bond.

In the compound (1), two $R^2$s may be the same or different, and are preferably the same in terms of manufacturability.

Examples of the compound in which Q is a single bond in of the compounds (1) and (2) include compounds represented by the following general formulas (1a) and (2a).

(1a)

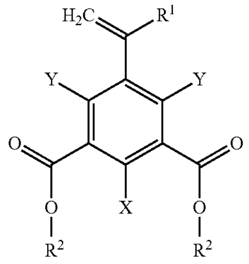

Here, in the general formula (1a), substituents $R^1$, $R^2$, X and Y represent the same groups as those in the explanation of the above general formula (1).

(2a)

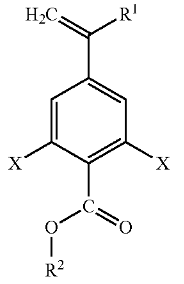

Here, in the general formula (2a), substituents $R^1$, $R^2$, and X represent the same groups as those in the explanation of the above general formula (2).

A method of synthesizing the compounds (1a) and (2a) is not particularly limited. Concretely, the compound (1a) can be synthesized, for example, by obtaining a precursor of the compound (1a) in which $R^2$ in the general formula (1a) is a hydrogen atom by a known method, and substituting the hydrogen atom by an ethyl group, an n-propyl group, an isopropyl group, an n-butyl group, an isobutyl group, an s-butyl group, or a t-butyl group. Examples of the compound (1a) are listed and explained below. The compound (2a) in which only the substituent is different can also be produced by a similar synthesis operation.

For example, in a case where $R^1$ is a hydrogen atom, X is a methyl group, and Y is a hydrogen atom in the compound (1a), the precursor can be synthesized by the following production process according to a report from Yiding Xu and others (Macromolecules 2009, 42(7), 2542-2550). First, an example of obtaining the compound (1a) ($R^1$ is a hydrogen atom, X is a methyl group, and Y is a hydrogen atom) from the process of obtaining the precursor according to the above report is indicated in a reaction scheme (1) mentioned below. Note that in the reaction scheme (1), the precursor is represented by a chemical structural formula F. In the reaction scheme (1), $R^2$ has the same meaning as $R^2$ in the above general formula (1a).

Reaction path (1)

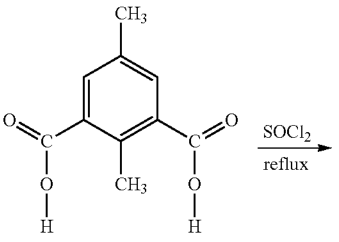

A

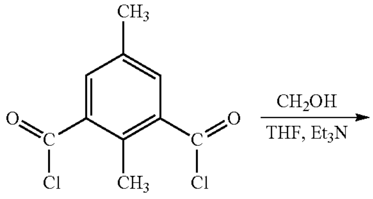

B

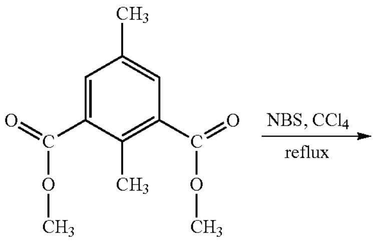

C

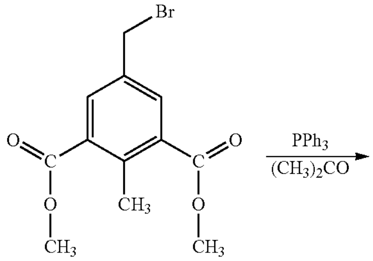

D

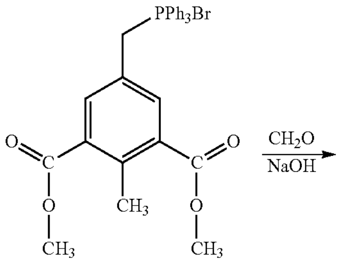

E

-continued

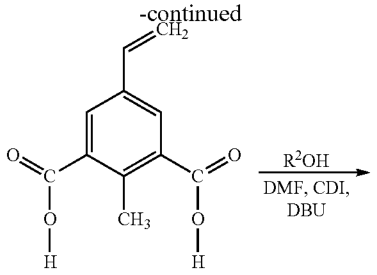

F

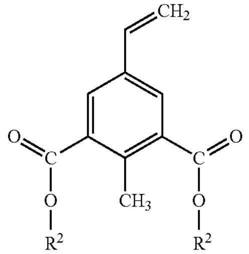

(1a)
$R^1 = H$
$X = CH_3$
$Y = H$

In the reaction scheme (1), for example, a compound A (2,5-dimethyl-1,3-dicarboxylic acid)benzene is used as a starting material. First, thionyl chloride is made to react on the compound A through reflux to obtain a compound B (2,5-dimethyl-1,3-dicarboxylic acid dichloride)benzene. Next, methanol is made to react on the compound B in the presence of triethylamine into a compound C (2,5-dimethyl-1,3-dimethyl dicarboxylate)benzene to protect carboxylic acid. Further, N-bromosuccinimide (NBS) is made to react on the compound C in a carbon tetrachloride to brominate the methyl group at the 5 position into a benzylbromo derivative (a compound D), and then triphenylphosphine ($PPh_3$) is made to react on the compound D to obtain a compound E (a benzyltriphenylphosphonium bromide derivative).

A vinyl group is formed in the compound E by formaldehyde in the presence of sodium hydroxide and, at the same time, deprotection of the dicarboxylic acid protected by the methyl group is performed, to obtain a compound F (2-methyl-5-vinyl-1,3-dicarboxylic acid)benzene as the precursor of the compound (1) ($R^1$ is a hydrogen atom).

In N,N-dimethyl formaldehyde (DMF), the obtained (2-methyl-5-vinyl-1,3-dicarboxylic acid)benzene is made to coexist with N,N'-carbonyldiimidazole (CDI) in a small excess, and alcohol represented by $R^2OH$ is made to react at room temperature in the presence of 1,8-diazabicyclo [5.4.0]-7-undecen (DBU) to obtain 2-methyl-5-vinyl-1,3-bisalkylisophthalic acid (alkyl group is $R_2$). The alcohol represented by $R^2OH$ is not limited, but is particularly preferably primary alcohol or secondary alcohol, and more preferably secondary alcohol. More specifically, preferable examples of the alcohol is ethanol, isopropyl alcohol, s-butyl alcohol, and the like.

Examples of the compound in which Q is a group expressed by —COO—$CH_2$— in the above compounds (1) and (2) include compounds represented by the following general formulas (1b) and (2b).

(1b)

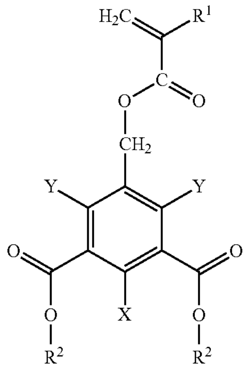

Here, in the general formula (1b), substituents $R^1$, $R^2$, X and Y represent the same groups as those in the explanation of the above general formula (1).

(2b)

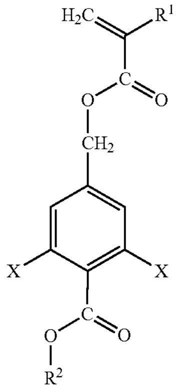

Here, in the general formula (2b), substituents $R^1$, $R^2$, and X represent the same groups as those in the explanation of the above general formula (2).

A method of synthesizing the compounds (1b) and (2b) is not particularly limited. For example, when X is a methyl group and Y is a hydrogen atom in the compound (1b), concretely, the compound (1b) can be produced by making a compound I ((meth)acrylic acid chloride) react with, for example, a compound G (4-methyl-3,5-dicarboxylic acid dialkyl ester)benzylalcohol (alkyl group is $R^2$) in the presence of triethylamine according to the following reaction formula (2) using a publicly known reaction such as an acid chloride reaction.

Further, the compound G can be (4-methyl-3,5-dicarboxylic acid dialkyl ester)phenol (alkyl group is $R^2$). In this case Q in the obtained compound (1) is —COO—.

Reaction formula (2)

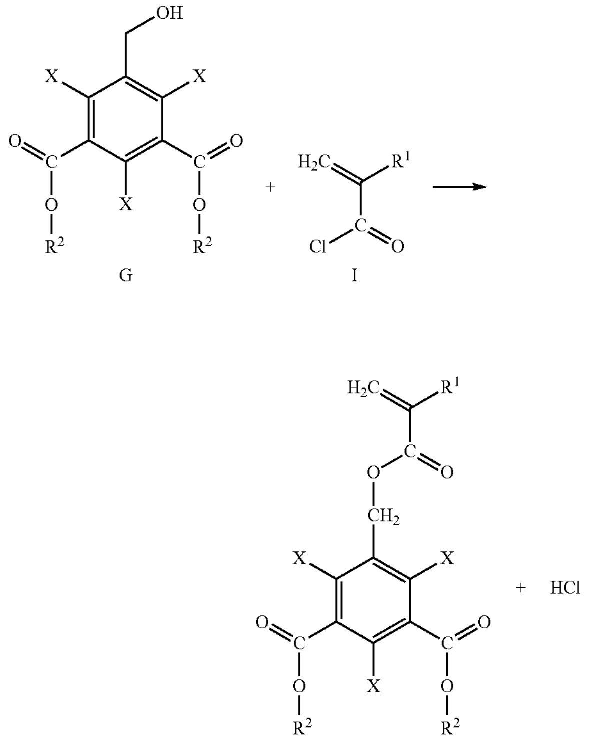

(1b)
$R^1$ = H
X = $CH_3$
Y = H

The compound G can be obtained by dissolving the aforementioned compound D as a starting material into a mixed solvent of acetone and water, making the resultant interact with an ion-exchange resin to form into (4-methyl-3,5-dicarboxylic acid)benzylalcohol (compound P), making CDI coexist in a small excess in DMF, and making the alcohol represented by $R^2OH$ react at room temperature in the presence of DBU.

In the reaction formula (2), $R^1$ and $R^2$ have the same meanings as $R^1$ and $R^2$ in the above general formula (1). Note that (meth)acrylic acid in this specification is a generic name of acrylic acid and methacrylic acid. The (meth) acrylate is a generic name of acrylate and methacrylate.

[Polymer]

A polymer of the embodiment is a polymer (hereinafter, also mentioned as a polymer 1) including the monomer unit (1) derived from the compound represented by the compound (1) and/or a polymer (hereinafter, also mentioned as a polymer 2) including a monomer unit (2) derived from the compound represented by the compound (2).

(Polymer 1)

The polymer 1 needs to be a polymer containing the monomer unit (1) (the same as the monomer unit (3) represented by the following general formula (3)) derived from the compound (1) in all monomer units constituting the polymer 1.

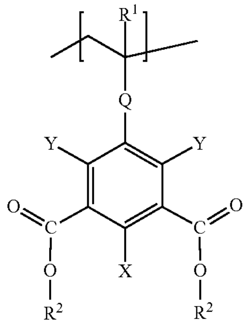

(3)

Note that $R^1$, $R^2$, Q, X, and Y are the same as those in the above general formula (1).

More specifically, the polymer 1 preferably contains at least one kind selected from a monomer unit (1a) derived from the compound represented by the compound (1a) and a monomer unit (1b) derived from the compound represented by the compound (1b). In other words, the polymer 1 may be a polymer (hereinafter, a polymer 1a) containing the monomer unit (1a) and not containing the monomer unit (1b), may be a polymer (hereinafter, a polymer 1b) containing the monomer unit (1b) and not containing the monomer unit (1a), or may be a polymer (hereinafter, a polymer 1ab) containing both the monomer unit (1a) and the monomer unit (1b).

The polymer 1a may contain only one kind of the monomer unit (1a) or may contain two or more kinds of the monomer units (1a). A content ratio of the monomer unit (1a) in the polymer 1a is preferably 50 to 100 mol % and more preferably 90 to 100 mol % with respect to all the monomer units constituting the polymer 1a.

Similarly, the polymer 1b may contain only one kind of the monomer unit (1b) or may contain two or more kinds of the monomer units (1b). A content ratio of the monomer unit (1b) in the polymer 1b is preferably 50 to 100 mol % and more preferably 90 to 100 mol % with respect to all the monomer units constituting the polymer 1b.

Each of the monomer unit (1a) and the monomer unit (1b) contained in the polymer 1ab may be only one kind or may be two or more kinds. A total content ratio of the monomer unit (1a) and the monomer unit (1b) in the polymer 1ab is preferably 50 to 100 mol % and more preferably 90 to 100 mol % with respect to all the monomer units constituting the polymer 1ab.

When the polymer 1 contains a monomer unit other than the monomer unit (1a) and the monomer unit (1b), the other monomer unit is not particularly limited. Examples of the other monomer unit include styrene, methyl methacrylate, glycidyl methacrylate, methacrylic acid, acrylic acid, and the like.

The synthesis of the polymer 1 can be performed by a normal method such as, for example, bulk polymerization, solution polymerization, emulsion polymerization, or suspension polymerization using constituent monomers of the monomer unit. The solution polymerization is preferred in terms of redissolution in a solvent after polymerization and removal of impurities such as an emulsifier and moisture as much as possible. When the polymer 1 is synthesized by the solution polymerization, normally, predetermined monomers are dissolved in a polymerization solvent and polymerized in the presence of a polymerization initiator. Polymerization conditions such as an amount of the polymerization solvent, polymerization temperature, and polymerization time are appropriately selected according to the kind of the monomer, a molecular weight of the polymer 1 to be synthesized, and the like.

(Polymer 2)

The polymer 2 only needs to be a polymer containing the monomer unit (2) (the same as a monomer unit (4) represented by the following general formula (4)) derived from the compound (2) in all monomer units constituting the polymer 2.

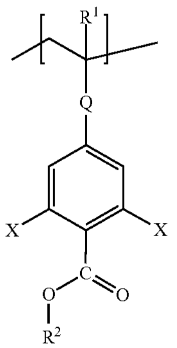

(4)

Note that $R^1$, $R^2$, Q, and X are the same as those in the above general formula (2).

More specifically, the polymer 2 preferably contains at least one kind selected from a monomer unit (2a) derived from the compound represented by the compound (2a) and a monomer unit (2b) derived from the compound represented by the compound (2b). In other words, the polymer 2 may be a polymer (hereinafter, a polymer 2a) containing the monomer unit (2a) and not containing the monomer unit (2b), may be a polymer (hereinafter, a polymer 2b) containing the monomer unit (2b) and not containing the monomer unit (2a), or may be a polymer (hereinafter, a polymer 2ab) containing both the monomer unit (2a) and the monomer unit (2b).

The polymer 2a may contain only one kind of the monomer unit (2a) or may contain two or more kinds of monomer units (2a). A content ratio of the monomer unit (2a) in the polymer 2a is preferably 50 to 100 mol % and more preferably 90 to 100 mol % with respect to all the monomer units constituting the polymer 2a.

Similarly, the polymer 2b may contain only one kind of the monomer unit (2b) or may contain two or more kinds of monomer units (2b). A content ratio of the monomer unit (2b) in the polymer 2b is preferably 50 to 100 mol % and more preferably 90 to 100 mol % with respect to all the monomer units constituting the polymer 2b.

Each of the monomer unit (2a) and the monomer unit (2b) contained in the polymer 2ab may be only one kind or may be two or more kinds. A total content ratio of the monomer unit (2a) and the monomer unit (2b) in the polymer 2ab is preferably 50 to 100 mol % and more preferably 90 to 100 mol % with respect to all monomer units constituting the polymer 2ab.

When the polymer 2 contains a monomer unit other than the monomer unit (2a) and the monomer unit (2b), the other monomer unit is not particularly limited. Examples of the other monomer unit include styrene, methyl methacrylate, glycidyl methacrylate, methacrylic acid, acrylic acid, and the like.

The synthesis of the polymer 2 can be performed by a normal method such as, for example, bulk polymerization, solution polymerization, emulsion polymerization, or suspension polymerization using constituent monomers of the monomer unit. The solution polymerization is preferred in terms of redissolution in a solvent after polymerization and removal of impurities such as an emulsifier and moisture as much as possible. When the polymer 2 is synthesized by the solution polymerization, normally, predetermined monomers are dissolved in a polymerization solvent and polymerized in the presence of a polymerization initiator. Polymerization conditions such as an amount of the polymerization solvent, polymerization temperature, and polymerization time are appropriately selected according to the kind of the monomer, a molecular weight of the polymer 2 to be synthesized, and the like.

[Pattern Forming Material]

A pattern forming material of the embodiment (hereinafter, mentioned as "this pattern forming material") is a pattern forming material containing a polymer (hereinafter, also mentioned as a polymer Z) including the monomer unit (3) represented by the above general formula (3) and/or the monomer unit (4) represented by the above general formula (4). This can also be said a pattern forming material containing a polymer including the monomer unit (1) derived from the compound (1) and/or the monomer unit (2) derived from the compound (2) in terms of the above correspondence.

The monomer unit (3) and the monomer unit (4) have side chains as mentioned above, and thereby provide a composite film in which a metallic compound is firmly bonded to an organic film obtained from this pattern forming material as explained below.

This pattern forming material is used to form an organic film on a film to be processed of a substrate having the film to be processed. This pattern forming material is contained in a later-explained composition for pattern formation of the embodiment together with, for example, an organic solvent, and applied on the film to be processed by using the composition to form the organic film.

The organic film may be formed of this pattern forming material itself or may be formed by the reaction of components contained in this pattern forming material. After the organic film is patterned, a metallic compound is bonded to the monomer unit (3) and/or the monomer unit (4) of the organic film to form a composite film. Then, the composite film is used as a mask pattern, and the above film to be processed is processed.

In the polymer Z, the reaction in which the metallic compound is bonded to the monomer unit (3) and/or the monomer unit (4) is expressed by a reaction represented by a reaction formula (F) or a reaction formula (G) mentioned below, for example, when taking the monomer unit (3) as an example. In each of these reaction formulas, $R^1$, Q, X and Y have the same meanings as $R^1$, Q, X and Y in the general formula (3), and n represents the number of repetitions of the monomer unit (3) in the polymer Z. In this regard, the metallic compound is bonded also to the monomer unit (4) by the same reaction.

The reactions represented by the reaction formula (F) and the reaction formula (G) are reaction examples in a case of using trimethylaluminum (TMA) as the metallic compound. $R^2$ in the monomer unit (3) is represented by $—CR^{11}R^{12}R^{13}$ (where $R^{11}$, $R^{12}$, and $R^{13}$ each independently represent a hydrogen atom or a hydrocarbon group, at least one of these is the hydrocarbon group, and the total carbon number of these is 1 to 13). In the reaction formula (F) and the reaction formula (G), the bonding of TMA to the monomer unit (3) is explained with RH of the monomer unit (3) set as the hydrocarbon group, $R^{12}$ and $R^{13}$ each set as the hydrogen atom or the hydrocarbon group.

As represented by the reaction formula (F), when TMA is made to react with the monomer unit (3) in the polymer Z, Al of TMA is coordinated to an electron lone pair of oxygen atoms of two carbonyl groups of the monomer unit (3). In this event, the bonding strength to a primary, secondary or tertiary hydrocarbon group ($—CR^{11}R^{12}R^{13}$) ester-bonded to a side-chain terminal of the monomer unit (3) is presumed to weaken. As a result, each $—CR^{11}R^{12}R^{13}$ is cleaved off from the monomer unit (3), whereby a monomer unit represented by a general formula (3') in which Al of TMA is bonded to two oxygen atoms derived from the ester bond is formed.

The leaving hydrocarbon group is converted to $R^{11'}{=}CR^{12}R^{13}$ in the reaction formula (F). Here, $R^{11'}$ is a group in which one hydrogen atom has fallen off from RH.

Though a leaving group is described as $R^{11'}{=}CR^{12}R^{13}$ in the reaction formula (F) for convenience, there can also be cases of $R^{11}C{=}R^{12'}R^{13}$ ($R^{12'}$ is a group in which one hydrogen atom has fallen off from $R^{12}$) and $R^{11}C{=}R^{13'}R^{12}$ ($R^{13'}$ is a group in which one hydrogen atom has fallen off from $R^{13}$). Thus, a hydrogen atom comes off from the leaving group to become alkene, which is cleaved off from the monomer unit. It is assumed that hydrogen which has come off the leaving group is substituted by a methyl group of TMA and leaves TMA as methane.

When the metallic compound is bonded to the monomer unit (3) in the polymer Z, the leaving hydrocarbon group can also be considered to take the reaction represented by the following reaction formula (G) aside from a process of the reaction formula (F). More specifically, as represented by the reaction formula (G), it can be thought that the hydrocarbon group leaves the monomer unit (3) as $R^{11}C{+}R^{12}R^{13}$ for convenience, and is then bonded to $(CH_3)^-$ leaving TMA to form into $R^{11}C(CH_3)R^{12}R^{13}$, and leaves the main chain.

Reaction formula (F)

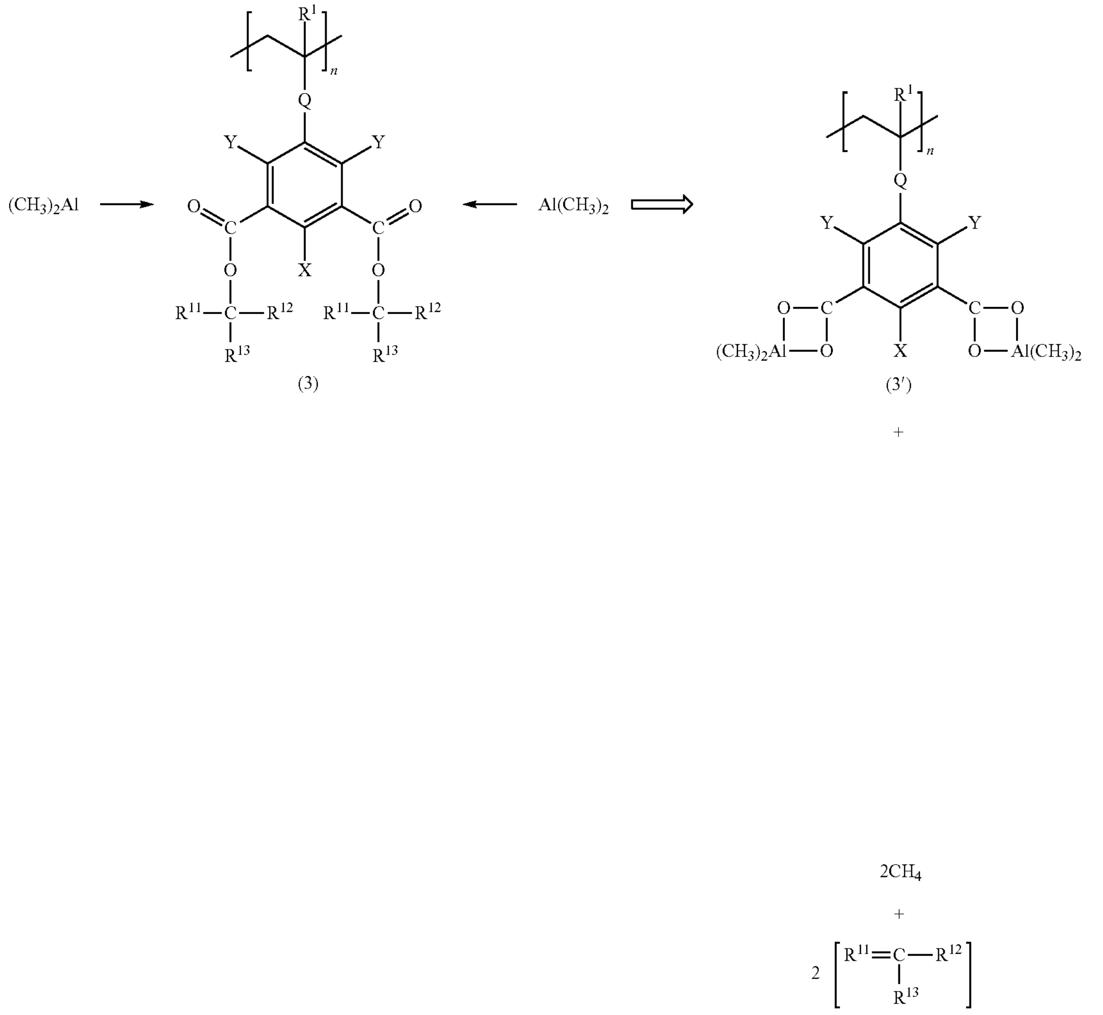

(3)

(3')

Reaction formula (G)

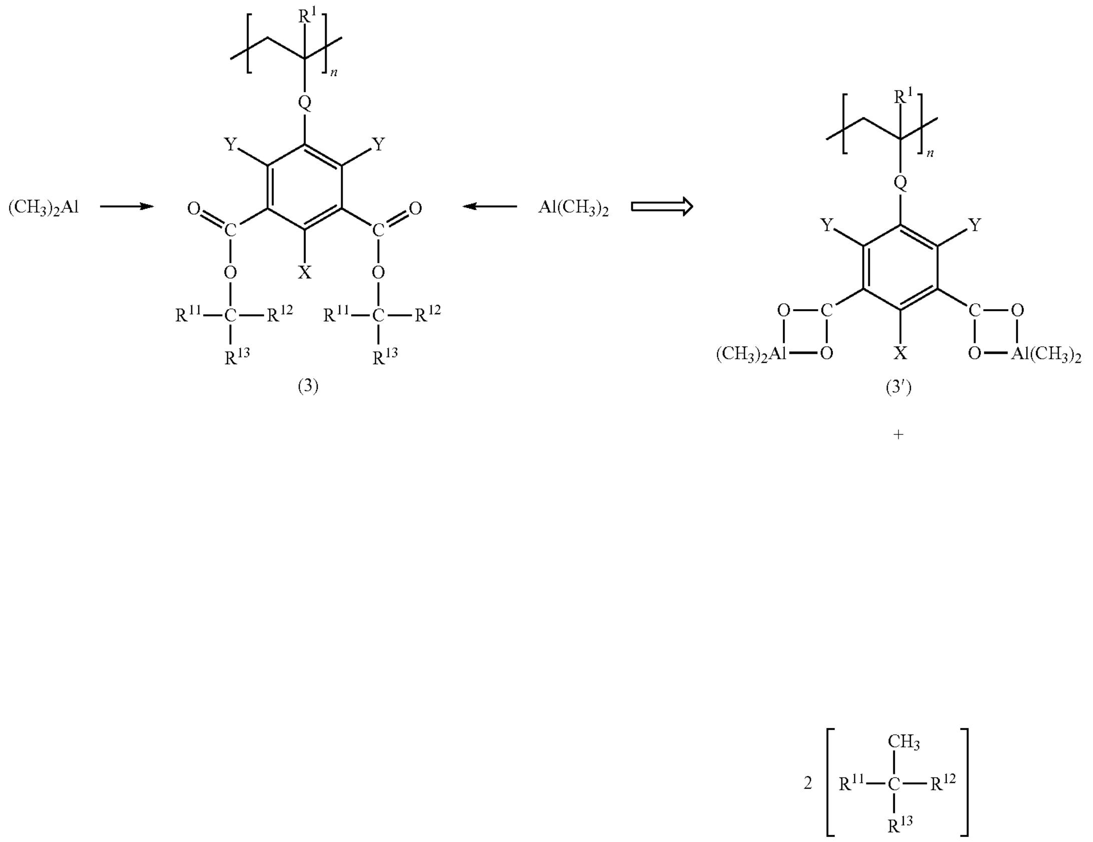

(3) (3')

The primary, secondary or tertiary hydrocarbon group ($R^2$) bonded to the side-chain terminal of the monomer unit (3) by ester is cleaved off under a specific condition even in a case where the metallic compound such as TMA is not adsorbed to the carbonyl group of the monomer unit (3). However, as represented by the reaction formula (F), when the metallic compound such as TMA is coordinated to the carbonyl group of the monomer unit (3), the leaving of the hydrocarbon group ($R^2$ (represented by $-CR^{11}R^{12}R^{13}$ in the reaction formula (F)) can be achieved under a significantly milder condition than the above specific condition. This is an event newly verified by the present inventors, and it can be said that the metallization of the organic film formed by using this pattern forming material allows the metallic compound to be firmly bonded and also achieves excellent productivity.

Note that the metallization is performed with respect to the organic film formed by using this pattern forming material in the embodiment. The organic film formed by using this pattern forming material may be formed of this pattern forming material itself or may be formed by the reaction of the components contained in this pattern forming material as explained above.

In this pattern forming material, the organic film formed from the polymer Z preferably has at least the structure of the side chain of the monomer unit selected from the monomer unit (3) and the monomer unit (4) as it is. This ensures that the composite film obtained by metallizing the organic film has, for example, a structure in which $Al(CH_3)_X$ (where X is a number of 0 to 2 and is 2 in the monomer unit (3')) being the metallic compound is firmly bonded to two oxygen atoms of the monomer unit (3') as represented by the monomer unit (3').

Besides, for example, a form in which $Al(CH_3)$ derived from TMA ($Al(CH_3)_3$) being the metallic compound as represented by the following general formula (5) is held by two carbonyl groups is also conceivable. This case is considered to form firmer bonding than the case where $Al(CH_3)_2$ is held by one carbonyl group as represented by the general formula (3') in each of the reaction formulas (F) and (G). Note that the number of coordinated carbonyl groups depends on the kind of a metal and steric hindrance of a polymer matrix surrounding the center metal. In the general formula (5), $R^1$, Q, X, and Y have the same meanings as $R^1$, Q, X, and Y in the general formula (3), and n represents the number of repetitions of the monomer unit (3) in the polymer Z.

(5)

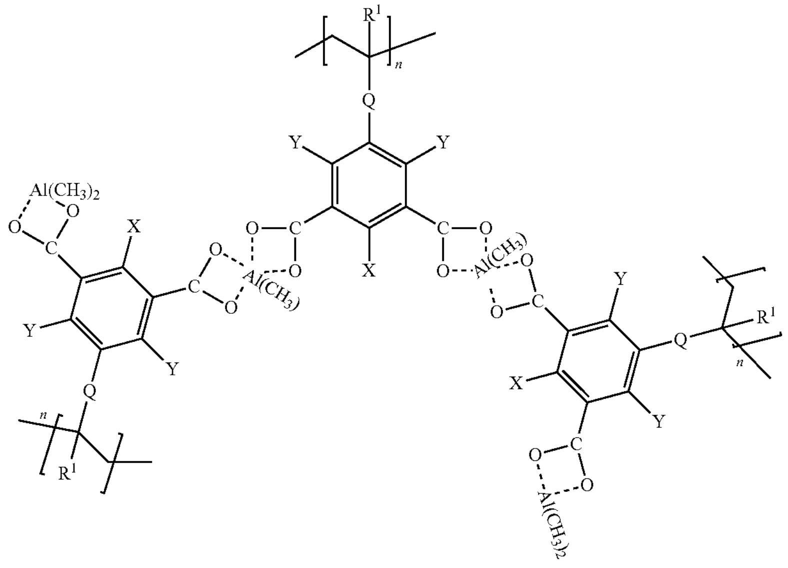

In the monomer unit (3), α carbon of $R^2$ is primary carbon, secondary carbon, or tertiary carbon. $R^2$ is explained while using a case where $R^2$ is represented by $—CR^{11}R^{12}R^{13}$ (where $R^{11}$, $R^{12}$ and $R^{13}$ each independently represent a hydrogen atom or a hydrocarbon group, at least one of these is the hydrocarbon group, and the total carbon number of these is 1 to 13) as an example.

When C in $—CR^{11}R^{12}R^{13}$ is the primary carbon, any one of $R^{11}$, $R^{12}$, and $R^{13}$ is the hydrocarbon group, and the remaining two are the hydrogen atoms. When C in $—CR^{11}R^{12}R^{13}$ is the secondary carbon, any two of $R^{11}$, $R^{12}$, and $R^{13}$ are the hydrocarbon groups, and the remaining one is the hydrogen atom. When C in $—CR^{11}R^{12}R^{13}$ is the tertiary carbon, all of $R^{11}$, $R^{12}$, and $R^{13}$ are the hydrocarbon groups. Note that the total carbon number of $R^{11}$, $R^{12}$, and $R^{13}$ is 1 to 13, and the total carbon number as $—CR^{11}R^{12}R^{13}$ is 2 to 14.

The present inventors have verified that in a case of a monomer unit in which the group ($R^2$) ester-bonded to the terminal of the side chain is $CH_3$ in the general formula (3), namely, in a case out of a scope of the embodiment, for example, in the metallization using TMA, Al of TMA is adsorbed to the electron lone pair of the oxygen atom of the carbonyl group, but a $CH_3$ group is difficult to be cleaved off from the terminal of the side chain. Accordingly, such a monomer unit cannot substantially take a structure of the monomer unit (3') in which Al of TMA is bonded to two oxygen atoms derived from the ester bond.

Note that the degree of metallization in the composite film can be verified by measuring an amount of metal of the metallic compound in the composite film by X-ray photoelectron spectroscopy (XPS). Further, the structure in which the metal of the metallic compound is bonded to two oxygen atoms derived from the ester bond at the terminal of the side chain of the monomer unit (3) in the organic film can be estimated by infrared spectroscopic analysis (IR). Absorption of carbonyl derived from ester can be detected in the organic film before the metallization, meanwhile the absorption is attenuated after the metallization, while a peak derived from carbonium ions is newly detected, thereby making it possible to presume that it is a structure in which the metal of the metallic compound is bonded to two oxygen atoms derived from the ester bond at the terminal of the side chain of the monomer unit (3) in the organic film.

Further, hydrocarbon obtained by cleaving of the terminal of the side chain of the monomer unit (3) in the metallization, for example, $R^{11'}=CR^{12}R^{13}$ in the reaction formula (F) is preferably removed from the composite film. For such purpose, the total carbon number of $R^{11}$, $R^{12}$ and $R^{13}$ is 1 to 13.

In a case where the composite film obtained by using this pattern forming material is used as a underlayer film of a later-explained layered mask structure, and when C in $—CR^{11}R^{12}R^{13}$ is the tertiary carbon, $—CR^{11}R^{12}R^{13}$ sometimes is cleaved off from the monomer unit (3) under a relatively mild condition. More specifically, in a case where an alternative layer is formed on the organic film as in the layered mask structure, and when C in $—CR^{11}R^{12}R^{13}$ is the tertiary carbon, $—CR^{11}R^{12}R^{13}$ in the organic film is possibly cleaved off when the layer is formed.

When $—CR^{11}R^{12}R^{13}$ of the monomer unit (3) is decomposed to form a carboxylic acid, the formed carboxylic acid becomes an acid catalyst, and when it is heated, a surrounding ester bond is further hydrolyzed. When C in $—CR^{11}R^{12}R^{13}$ is the primary carbon or secondary carbon, $—CR^{11}R^{12}R^{13}$ is more difficult to be cleave off as compared with the case of the tertiary carbon. Therefore, C in $—CR^{11}R^{12}R^{13}$ is sometimes preferably the primary carbon or the secondary carbon depending on a zone of temperature applied when the base film is produced.

When the α carbon is the tertiary carbon, $R^2$ in the monomer unit (3) is a t-butyl group. When the α carbon is the secondary carbon, $R^2$ is an isopropyl group or an s-butyl group. When the α carbon is the primary carbon, $R^2$ is an ethyl group, an n-propyl group, an n-butyl group, or an isobutyl group.

When C in $—CR^{11}R^{12}R^{13}$ is the tertiary carbon, concrete examples of $—CR^{11}R^{12}R^{13}$ include a hydrocarbon group in which $R^{11}$, $R^{12}$, and $R^{13}$ are each independently, for example, a methyl group, an ethyl group, a propyl group, a butyl group, a pentyl group, a hexyl group, a heptyl group, or an octyl group, and the total carbon number is 3 to 13.

Among these, the t-butyl group in which all of $R^{11}$, $R^{12}$, and $R^{13}$ are the methyl groups is preferred as $—CR^{11}R^{12}R^{13}$.

When C in $—CR^{11}R^{12}R^{13}$ is the secondary carbon, concrete examples of $—CR^{11}R^{12}R^{13}$ include the hydrocarbon group in which when $R^{13}$ is the hydrogen atom, $R^{11}$ and $R^{12}$ are each independently, for example, a methyl group, an ethyl group, a propyl group, a butyl group, a pentyl group, a hexyl group, a heptyl group, an octyl group, or a nonyl group, and the total carbon number is 2 to 13. Among these, the isopropyl group in which both of $R^{11}$ and $R^{12}$ are the methyl groups, the s-butyl group in which $R^{11}$ and $R^{12}$ are each the methyl group and the ethyl group, a 3-pentyl group in which $R^{11}$ and $R^{12}$ are each the ethyl group, a 4-heptyl group in which $R^{11}$ and $R^{12}$ are each the propyl group, or a 5-nonyl group in which $R^{11}$ and $R^{12}$ are each the n-butyl group is preferred as $—CR^{11}R^{12}R^{13}$ (where $R^{13}$ is H).

When C in $—CR^{11}R^{12}R^{13}$ is the primary carbon, concrete examples of $—CR^{11}R^{12}R^{13}$ include the hydrocarbon group in which when $R^{12}$ and $R^{13}$ are the hydrogen atoms, $R^{11}$ is, for example, a methyl group, an ethyl group, a propyl group, a butyl group, a pentyl group, a hexyl group, a heptyl group, an octyl group, a nonyl group, or a decyl group, and the total carbon number is 1 to 13. Among these, the ethyl group in which $R^{11}$ is the methyl group, or the propyl group in which $R^{11}$ is the ethyl group is preferred as $—CR^{11}R^{12}R^{13}$ (where $R^{12}$ and $R^{13}$ are H). The benzyl group is also preferred as $R^{11}$ in $—CR^{11}R^{12}R^{13}$ (where $R^{12}$ and $R^{13}$ are H).

Note that it has been explained in the above that TMA is coordinated to the oxygen atoms derived from the ester bond to form firm bonding, but if excessive TMA is coordinated to the oxygen atoms, there is a possibility to cause destabilization of the monomer unit (3). The destabilization is suppressed by setting at least one of the substituents X and Y to the hydrocarbon group in this embodiment. In other words, the benzene ring has a carbon atom bonded to the ester bond, and at least one of the other carbon atoms in the benzene ring, adjacent to the bonded carbon atom, has a $C_{1-4}$ hydrocarbon group as a substituent, thereby suppressing the coordination of excessive TMA to the oxygen atoms derived from the ester bond as compared with a case where all of X and Y in the monomer unit (3) are the hydrogen atoms. This ensures that the composite film obtained by using the pattern forming material having the monomer unit (3) has high etch resistance in later-explained etching.

Further, Q in the general formula (3) is the same as explained in the general formulas (1) and (2) as explained above. Note that this Q is preferably a single bond or a group expressed by $—COO—CH_2—$. When Q is a single bond in the general formula (3), it is a monomer unit (31) represented by the following general formula (31), and when Q is a $—COO—CH_2—$ group, it is a monomer unit (32) represented by the following general formula (32). Note that in the general formulas (31), (32), $R^1$, $R^2$, X, and Y have the same meanings as $R^1$, $R^2$, X, and Y in the general formula (3).

(31)

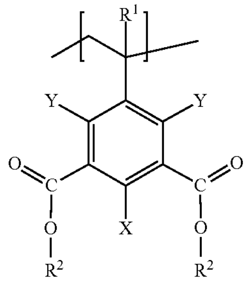

-continued (32)

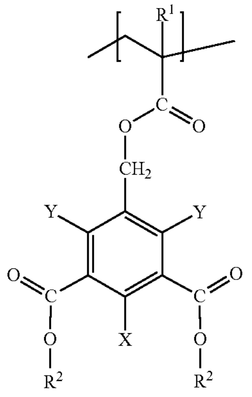

A compound in which $R^2$ is the ethyl group, the isopropyl group, the s-butyl group, or the t-butyl group among constituent monomers of the monomer unit (31) is preferable, and a compound in which $R^2$ is the ethyl group, the isopropyl group, the s-butyl group, or the t-butyl group among constituent monomers of the monomer unit (32) is preferable.

The polymer Z is the polymer including the monomer unit (3) and/or the monomer unit (4) as explained above. The polymer Z having the monomer unit (3) is explained below as an example, and the example is similarly applied also to the case of the polymer including the monomer unit (4).

The polymer Z may contain one kind of the monomer unit (3) or may contain two or more kinds of the monomer units (3). The polymer Z may be composed of only the monomer unit (3), or may be a copolymer of the monomer unit (3) and a monomer unit other than the monomer unit (3). A ratio of the monomer unit (3) in the polymer Z is preferably 50 mol % or more, more preferably 80 mol % or more, and further preferably 90 mol % or more with respect to all the monomer units of the polymer Z.

The polymer Z has the monomer unit (3), thereby making it possible to achieve both an excellent metallization property in the organic film obtained from this pattern forming material containing the polymer Z and high etch resistance in the obtained mask pattern. In terms of the metallization property and etch resistance as mentioned above, the ratio of the monomer unit (3) in the polymer Z is preferably 50 mol % or more, and the ratio is particularly preferably 100 mol % when later-explained other properties are not considered.

The synthesis of the polymer Z can be performed by a normal method such as, for example, bulk polymerization, solution polymerization, emulsion polymerization, or suspension polymerization, by using the constituent monomers of the monomer unit. The solution polymerization is preferred in terms of redissolution in a solvent after the polymerization, and prevention of contaminations by impurities such as an emulsifier and water moisture as much as possible. When the polymer Z is synthesized by the solution polymerization, normally, a predetermined monomer is dissolved in a polymerization solvent and polymerized in the presence of a polymerization initiator. The monomers used for the production of the polymer Z include the constituent monomers of the monomer unit (3). As explained later, when the polymer Z includes a monomer unit other than the monomer unit (3), constituent monomers of all the monomer units constituting the polymer Z are used for the polymerization. Polymerization conditions such as an amount of the polymerization solvent, a polymerization temperature, and a polymerization time are appropriately selected according to the kind of the monomer, a molecular weight of the polymer Z to be synthesized, and the like.

A weight-average molecular weight (Mw) of the polymer Z is preferably 1,000 to 1,000,000 [g/mol] (hereinafter, a unit is sometimes omitted), more preferably 2,000 to 1,000,000, and particularly preferably 2,000 to 100,000. The molecular weight (Mw) of the polymer Z can be measured by gel permeability chromatography (GPC).

Note that the metallic compound bonded to the organic film in the above may be thereafter appropriately processed and used as a mask pattern. For example, in a case of $Al(CH_3)_2$ shown in the reaction formula (F), the metallic compound is bonded to the organic film and then subjected to oxidation treatment to form aluminum hydroxide, aluminum oxide, or the like. The oxidation treatment is normally performed by using an oxidant such as water, ozone, or oxygen plasma. Note that the oxidation treatment may be naturally performed by moisture in an atmosphere without any special operation.

Further, an explanation has been made by exemplifying $Al(CH_3)_3$ as the metallic compound bonded to the organic film in the above, but an Al compound other than $Al(CH_3)_3$ is applicable, and it is possible to obtain similar bonding structures even in metallic compounds of metals other than Al such as, for example, Ti, V, W, Hf, Zr, Ta, and Mo.

The composite film obtained by using this pattern forming material has high etch resistance since the metallic compound is firmly bonded to the organic film. Examples of etching include reactive ion etching (RIE), ion beam etching (IBE), and the like, and it is possible to achieve sufficient resistance even in the IBE which requires particularly high resistance. Here, in order to achieve a processing shape having a high aspect ratio with respect to the film to be processed, the layered mask structure is sometimes employed in the mask pattern. The composite film formed by using this pattern forming material is suitably used as the base film to be formed between a resist film and the film to be processed when used for the layered mask structure.

Conventionally, in the layered mask structure aimed for high etch resistance, a carbon deposition layer obtained by a chemical vapor deposition (CVD) method has been used as the base film between the resist film and the film to be processed. The composite film formed by using this pattern forming material has advantages that materials thereof are inexpensive and a film can be easily formed while having a function capable of substituting for the carbon deposition layer obtained by using the very costly CVD method for forming a film.

In the polymer Z, this pattern forming material may contain the monomer unit other than the monomer unit (3) within a range of not impairing the effect of the embodiment in order to impart properties (hereinafter, also mentioned as "other properties") required in addition to the metallization property and the etch resistance as a material of forming the mask pattern.

Examples of the other properties required for the polymer Z include the property of making the obtained organic film difficult to be dissolved in the organic solvent. This is a particularly required property when this pattern forming material is applied to the layered mask structure. In the layered mask structure, the organic film formed by using this pattern forming material as explained above is preferably formed as the under layer film between the resist film and the film to be processed. In this case, normally, another layer constituting the layered mask is formed by a so-called wet coating method of dissolving a material composing the layer in the organic solvent or the like and applying the resultant onto the organic film. In this event, when the organic film formed by using the polymer Z is soluble to the organic solvent used in the wet coating method, there is a possibility that the organic film is partly dissolved to form a mixed layer mixed with composing materials of the layer to be formed on the organic film.

Hence, the present inventors have conceived that by introducing a crosslinkable monomer unit having a crosslinkable functional group at a terminal of a side chain to the polymer Z in addition to the monomer unit (3), elution of film components is suppressed in the obtained organic film. This makes it possible that the organic film formed by using the polymer Z is difficult to dissolve in the organic solvent, so that even when an alternative layer is formed by the wet coating method on the organic film, the mixed layer is hardly formed. Hereinafter, the polymer Z having the crosslinkable monomer unit in addition to the monomer unit (3) is sometimes mentioned as a crosslinkable polymer Z.

The crosslinkable functional group of the crosslinkable monomer unit is not particularly limited as long as it is a functional group having crosslinkability, but in terms of storage stability, a functional group exhibiting a crosslinking function by energy from the outside, for example, by heating or light irradiation is preferred. Examples of the crosslinkable functional group include a glycidyl group, an oxetanyl group, an amino group, an azido group, a thiol group, a hydroxyl group, a carboxyl group, and the like. The glycidyl group, the oxetanyl group, the hydroxyl group, the carboxyl group, and the protected carboxyl group are particularly preferred from the viewpoints that a structure after crosslinking is low in activity with respect to the metallic compound, and that energy required for a crosslinking reaction is relatively mild.

Examples of a constituent monomer of the crosslinkable monomer unit include a monomer in which a monovalent organic group having a crosslinkable functional group at a terminal is bonded to any carbon atom of an ethylene group. Concrete examples of the crosslinkable monomer unit include a monomer unit (6) represented by the following general formula (6).

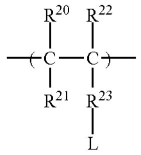
(6)

In the general formula (6), $R^{20}$, $R^{21}$, and $R^{22}$ are each independently a hydrogen atom or a $C_{1-10}$ hydrocarbon group, and $R^{23}$ is a single bond or a $C_{1-20}$ hydrocarbon group optionally including an oxygen atom, a nitrogen atom, or an ester bond between carbon-carbon atoms or at a bond terminal, and L is a crosslinkable functional group.

As the constituent monomer of the crosslinkable monomer unit, (meth)acrylate in which a compound having a crosslinkable functional group at a terminal is ester-bonded to (meth)acrylic acid or a styrene derivative in which a compound having a crosslinkable functional group at a terminal is substituted is preferred.

Concrete examples of (meth)acrylate having the glycidyl group among (meth)acrylates to be the constituent monomer of the crosslinkable monomer unit include a compound represented by the following general formula L1.

$H_2C{=}C(R^{31})—C({=}O)—O—(R^{32}—O)_m$-Gly L1

In the general formula L1, $R^{31}$ is a hydrogen atom or a methyl group, Gly is the glycidyl group, m is 0 to 3, and $R^{32}$ is a $C_{1-10}$ alkylene group. Concretely examples of (meth) acrylate represented by L1 include glycidyl (meth)acrylate represented by the following formula L1-1. In each of the following general formulas, $R^{31}$ is a hydrogen atom or a methyl group.

(L1-1)

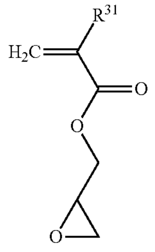

Concrete examples of (meth)acrylate having the oxetanyl group among (meth)acrylates to be the constituent monomer of the crosslinkable monomer unit include (3-ethyl-3-oxetanyl)methyl(meth)acrylate represented by the following general formula L2-1. In the following general formula, $R^{31}$ is a hydrogen atom or a methyl group.

(L2-1)

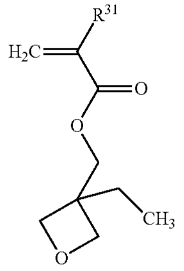

Concrete examples of the styrene derivative having the glycidyl group among styrene derivatives to be the constituent monomer of the crosslinkable monomer unit include a compound represented by the following general formula L3.

(L3)

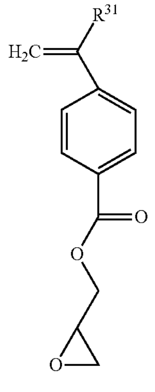

A copolymer of the monomer unit (1) and the crosslinkable monomer unit constituting the polymer Z is preferably rich in randomness, and it is only necessary to determine a combination of the monomer unit (1) and the crosslinkable monomer unit from the above viewpoint.

When the polymer Z contained in this pattern forming material contains the crosslinkable monomer unit, the polymer Z may contain only one kind of crosslinkable monomer unit, or may contain two or more kinds of crosslinkable monomer units. When the polymer Z contains one kind of monomer unit (3) and two or more kinds of crosslinkable monomer units, the polymer Z may be a mixture of two or more kinds of copolymers each including the monomer unit (3) and each of the crosslinkable monomer units, or may be one kind of copolymer including one kind of monomer unit (3) and two or more kinds of crosslinkable monomer units.

When the polymer Z contains two or more kinds of monomer units (3) and one kind of crosslinkable monomer unit, the polymer Z may be a mixture of two or more kinds of copolymers each including the crosslinkable monomer unit and each of the monomer units (3), or may be one kind of copolymer including two or more kinds of monomer units (3) and one kind of crosslinkable monomer unit.

When the polymer Z contains the monomer unit (3) and the crosslinkable monomer unit, the crosslinkable functional groups of the crosslinkable monomer units contained in different polymer chains react with each other to be bonded, resulting in that the main chains of a plurality of polymers are crosslinked to make it difficult to dissolve the polymer, regardless of whether the polymer Z is a mixture of two or more kinds of copolymers or is constituted by one kind of copolymer as explained above. Note that the reaction between the crosslinkable functional groups is preferably performed by, for example, heating, light irradiation, or the like when the organic film is formed.

A ratio of the crosslinkable monomer unit in the polymer Z is preferably 0.5 mol % or more and less than 20 mol %, more preferably 1 mol % or more and less than 10 mol %, and further preferably 2 mol % or more and less than 10 mol % to all the monomer units constituting the polymer Z.

When the ratio of the crosslinkable monomer unit is less than 0.5 mol % to all the monomer units, the crosslinking in the polymer Z cannot be sufficiently performed to fail to sufficiently make the polymer difficult to dissolve, resulting in a possibility that the component of the organic film is eluted to a wet coating solution used for forming an upper layer on the organic film. When the ratio of the crosslinkable monomer unit is 20 mol % or more to all the monomer units, there is a possibility that the crosslink density becomes too high to suppress diffusion of the metallic compound into the organic film and fail to metallize the organic film throughout the film volume.

Hereinafter, the crosslinkable polymer Z will be explained by exemplifying a case where the crosslinkable monomer unit is the monomer unit L1-1. The following explanation is applied to the crosslinkable polymer Z even when the crosslinkable monomer unit is crosslinkable monomer units other than the monomer unit L1-1.

A chemical structural formula Z11 mentioned below represents a chemical structural formula of the polymer Z constituted by combining the monomer unit (3) and the monomer unit L1-1. The polymer represented by the chemical structural formula Z11 is hereinafter mentioned as a polymer Z11. Hereinafter, other polymers are also expressed similarly. In the chemical structural formula Z11, $R^1$, $R^2$, Q, X, and Y have the same meanings as $R^1$, $R^2$, Q, X, and Y in the general formula (3), and $R^{31}$ is a hydrogen atom or a methyl group.

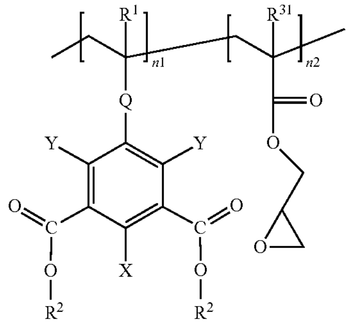

(Z11)

The polymer Z11 is constituted of the monomer unit (3) and the monomer unit L1-1. A molar ratio of the monomer unit L1-1 to all the monomer units in the polymer Z11 is represented by n2, and a molar ratio of the monomer unit (3) to all the monomer units in the polymer Z11 is represented by n1. A sum of n1 and n2 is 100 mol % in the polymer Z11. Note that in the polymer Z11, the monomer unit (3) and the monomer unit L1-1 may be alternately present, or may be randomly present. Preferably, the monomer units are uniformly present according to content ratios of the monomer units.

When the polymer Z contained in this pattern forming material is the crosslinkable polymer Z and constituted of only the polymer Z11, n2 in the polymer Z11 is preferably 0.5 mol % or more and less than 20 mol %, more preferably 1 mol % or more and less than 10 mol %, and further more preferably 2 mol % or more and less than 10 mol % similarly to the above explanation. Besides, n1 is preferably more than 80 mol % and 99.5 mol % or less, more preferably more than 90 mol % and 99 mol % or less, and further more preferably more than 90 mol % and 98 mol % or less.

Note that the crosslinkable polymer Z may be a mixture of the polymer Z11 and another crosslinkable polymer Z. When the crosslinkable polymer Z is the mixture of the polymer Z11 and the other crosslinkable polymer Z, content ratios of the monomer unit (3) and the crosslinkable monomer unit in each crosslinkable polymer do not necessarily fall within the above ranges. The content ratios of the monomer unit (3) and the crosslinkable monomer unit preferably fall within the above range as the entire mixture.

Adjustment of ratios of the monomer units in the crosslinkable polymer Z can be performed by adjusting ratios of monomers used at a time of polymerization. A molecular weight (Mw) of the crosslinkable polymer Z is preferably 1,000 to 100,000,000, and more preferably 2,000 to 100,000.

Conditions when the crosslinkable polymer Z is crosslinked depend on the kind of crosslinkable functional group of the crosslinkable monomer unit. For example, when the crosslinkable functional group is the glycidyl group or the oxetanyl group, the crosslinking is performed by opening an epoxy ring or an oxetane ring. Accordingly, the polymers Z are crosslinked by performing heating or light irradiation under the conditions that the epoxy ring or the oxetane ring is opened. A curing agent may be used to crosslink the polymer Z.

The curing agent has reactivity with respect to the crosslinkable functional group and allows the crosslinkable functional groups to be bonded to each other via the curing agent. The curing agent promotes a crosslinking reaction and makes the crosslinking of the polymers Z easy. Accordingly, a suitable curing agent is different depending on the kind of the crosslinkable monomer unit. For example, when the crosslinkable functional group of the crosslinkable monomer unit is the glycidyl group, an amine compound, a compound having an acid anhydride structure, a compound having a carboxylic acid, or a compound having a hydroxyl group can be suitably used as the curing agent.

The amine compound has a plurality of primary amines or secondary amines in a structure. Examples of the amine compound usable for the curing agent include ethylenediamine, trimethylenediamine, tetramethylenediamine, pentamethylenediamine, hexamethylenediamine, heptamethylenediamine, octamethylenediamine, nonamethylenediamine, decamethylenediamine, diethylenetriamine, triethylenetetramine, tetraethylenepentamine, pentaethylenehexamine, 1,2-diaminocyclohexane, 1,3-diaminocyclohexane, 1,4-diaminocyclohexane, o-phenylenediamine, m-phenylenediamine, p-phenylenediamine, m-xylenediamine, p-xylenediamine, isophorondiamine, 4,4'-methylenedianiline, diaminodiphenylsulfone, diaminodiphenyl ether, and the like.

Examples of the compound having the acid anhydride structure usable for the curing agent include hexahydrophthalic anhydride, 4-methylhexahydrophthalic anhydride, succinic anhydride, itaconic anhydride, dodecenylsuccinic anhydride, and the like.

Examples of the compound having the carboxylic acid usable for the curing agent include hexahydrophthalic acid, 4-methylhexahydrophthalic acid, succinic acid, itaconic acid, dodecenylsuccinic acid, citric acid, terephthalic acid, and the like.

The compound having the hydroxyl group includes a plurality of hydroxyl groups in a structure. Examples of the compound having the hydroxyl group usable for the curing agent include polyphenol, 1,4-benzenediol, 1,3-benzenediol, 1,2-benzenediol, ethylene glycol, and the like.

A curing accelerator having tertiary amine may be added in order to enhance the reactivity of the curing agents other than the above amine compound. Examples of the curing accelerator include cyandiamide, 1,8-diazabicyclo[5.4.0]-undecene-7, 1,5-diazabicyclo[4.3.0]-nonene-5, tris(dimethylaminomethyl)phenol, ethylene glycol, and the like.

When this pattern forming material contains the curing agent together with the crosslinkable polymer Z, the amount of the curing agent is preferably an amount that a ratio of a group reactive to the crosslinkable functional group of the curing agent is 0.01 to 1 mol with respect to 1 mol of the crosslinkable functional group of the crosslinkable polymer Z.

The polymer Z contained in this pattern forming material may further include another monomer unit (hereinafter, mentioned as "a different monomer unit") other than the monomer unit (3) and the crosslinkable monomer unit as necessary. The polymer Z has the alternative monomer unit and thereby makes it possible to adjust solubility of the polymer Z to the organic solvent, film formability in coating, a glass transition temperature of the film after coating, heat resistance, and the like.

Examples of a monomer constituting the different monomer unit include styrene, 1-vinylnaphthalene, 2-vinylnaphthalene, 9-vinylanthracene, vinylbenzophenone, hydroxystyrene, methyl (meth)acrylate, (meth)acrylic acid, methyl 4-vinyl benzonate, 4-vinyl benzoic acid, a monomer represented by the following general formula (7), and the like. The alternative monomer unit can be constituted of at least any one of these monomers.

(7)

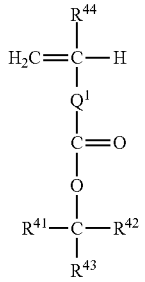

In the general formula (7), $R^{41}$, $R^{42}$, and $R^{43}$ each independently represent a hydrogen atom or a hydrocarbon group optionally including an oxygen atom, at least one of these is the hydrocarbon group, the total carbon number of these is 1 to 13, and these may be bonded to each other to form a ring. $R^{44}$ is the hydrogen atom or a methyl group. $Q^1$ is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom.

An abundance ratio of the alternative monomer unit is preferably 50 mol % or less, more preferably 10 mol % or less, and further preferably 1 mol % or less to all the monomer units constituting the polymer Z. Setting the ratio of the alternative monomer unit to 50 mol % or less makes it possible to keep the content of the monomer unit (3) in the organic film high, and firmly bond a larger amount of the metallic compound in the organic film.

This pattern forming material may contain a component other than the polymer Z as necessary within a range of not impairing the effect of this embodiment in addition to the polymer Z. Typical examples of the component other than the polymer Z include the above curing agent and curing accelerator. Examples of a component other than the curing agent and the curing accelerator include a thermal acid generator, a photoacid generator, and the like. A content of the component other than the polymer Z in this pattern forming material can be appropriately selected according to each of the components. For example, the content of the curing agent is as explained above. The content of the component excluding the polymer Z other than the curing agent is preferably 1 wt % or less, and more preferably 0.1 wt % or less to the total amount of the pattern forming material.

A method of forming the organic film by using this pattern forming material may be a dry coating method or a wet coating method. When the organic film is formed by the dry coating method, the organic film can be formed by the dry coating method, for example, a vapor disposition method by using this pattern forming material itself. When the organic film is formed by the wet coating method, a method of applying a composition containing this pattern forming material and an organic solvent onto the film to be processed and drying it to form the organic film is preferred.

(Embodiment of Composition for Pattern Formation)

A composition for pattern formation (hereinafter, also simply mentioned as a "composition") of the embodiment is a composition containing a pattern forming material for forming an organic film, the organic film being formed using the pattern forming material on a film to be processed of a substrate having the film to be processed, and the organic film being patterned and then impregnated with a metallic compound to form a composite film which is used as a mask pattern when processing the film to be processed, the composition containing the pattern forming material containing a polymer including the monomer unit (3) represented by the above general formula (3) and/or the monomer unit (4) represented by the above general formula (4) and an organic solvent capable of dissolving the pattern forming material.

This pattern forming material can be used as the pattern forming material in the composition of the embodiment. The composition of the embodiment can be used for a use similar to that of the one explained above in this pattern forming material. The organic solvent in the composition of the embodiment is not particularly limited as long as it is an organic solvent dissolving this pattern forming material, particularly, the polymer Z contained in this pattern forming material.

Examples of the organic solvent dissolving the polymer Z include aromatic hydrocarbons such as toluene, xylene, and mesitylene, ketones such as cyclohexanone, acetone, ethyl methyl ketone, and methyl isobutyl ketone, and cellosolves such as methyl cellosolve, methyl cellosolve acetate, ethyl cellosolve acetate, butyl cellosolve acetate, and propylene glycol monomethyl ether acetate (PGMEA), and the cellosolves are preferred. The organic solvent can be used by combining two or more kinds of them as necessary.

A content of the pattern forming material in the composition of the embodiment is preferably 1 to 30 wt %, more preferably 1 to 20 wt %, and further preferably 1 to 15 wt % to the entire composition. A content of the organic solvent in the composition of the embodiment is preferably 70 to 99 wt %, more preferably 80 to 99 wt %, and further preferably 85 to 99 wt % to the entire composition. The content of each of the pattern forming material and the organic solvent in the composition of the embodiment falls within the above range, thereby making it possible to form the organic film onto the film to be processed by the wet coating method.

A normal method is applicable as a method of applying the composition of the embodiment onto the film to be processed by the wet coating method. Concretely, spin coating or dip coating is preferred. Thereafter, the organic solvent is removed from a coating of the composition by drying, whereby the organic film can be formed. When the polymer Z is the crosslinkable polymer Z, a crosslinking treatment according to the crosslinkable polymer Z used in forming the organic film, for example, heating or light irradiation is performed to cause crosslinking.

Here, when the organic film is formed by using the composition of the embodiment, the organic film is preferably formed under a condition that $R^2$ is not cleaved off from the monomer unit (3) or the monomer unit (4). If $R^2$ is cleaved off from the monomer unit (3) or the monomer unit (4) in forming the organic film, there is a possibility that uniform metallization does not occur in a film thickness direction in metallization to be performed later. It is highly likely that a firm bond between the organic film and the metallic compound cannot be achieved.

(Embodiment of Pattern Forming Method and Method of Manufacturing Semiconductor Device)

A pattern forming method of the embodiment has processes of (A1) to (C) mentioned below.

(A1) A process of forming an organic film on a substrate by using the pattern forming material containing the polymer including the monomer unit (3) and/or the monomer unit (4)

(B) A process of patterning the organic film obtained in the process of (A1)

(C) A process of infiltrating the patterned organic film with a metallic compound to form a composite film so as to obtain a mask pattern formed of the composite film A method of manufacturing a semiconductor device of the embodiment has processes of (A) to (D) mentioned below.

(A) A process of forming an organic film on a film to be processed of a substrate having the film to be processed by using the pattern forming material containing the polymer including the monomer unit (3) and/or the monomer unit (4)

(B) A process of patterning the organic film obtained in the process of (A)

(C) A process of infiltrating the patterned organic film with a metallic compound to form a composite film so as to obtain a mask pattern formed of the composite film (D) A process of processing the film to be processed by using the mask pattern This pattern forming material explained above is applicable as the pattern forming material to be used in the pattern forming method and the method of manufacturing the semiconductor device of the embodiment.

Hereinafter, the method of manufacturing the semiconductor device of the embodiment is explained using FIG. 1A to FIG. 1E. Here, the processes of (A1), (B), and (C) in the pattern forming method of the embodiment correspond to the processes of (A), (B), and (C) in the method of manufacturing the semiconductor device of the embodiment, respectively. Accordingly, to each of the processes of (A1), (B), and (C) in the pattern forming method of the embodiment, a concrete method of each of the processes of (A), (B), and (C) in the method of manufacturing the semiconductor device explained below can be similarly applied.

FIG. 1A to FIG. 1E are sectional views each illustrating one process of the method of manufacturing the semiconductor device according to the embodiment. In the method of manufacturing the semiconductor device of the embodiment, the processes progress in order of FIG. 1A to FIG. 1E.

FIG. 1A is a sectional view schematically illustrating the process (A), namely, the process of forming the organic film on the film to be processed of the substrate having the film to be processed by using the pattern forming material. In this embodiment, an organic film 3 is formed by use of the pattern forming material in order to process a film to be processed 2 formed on a semiconductor substrate 1.

In the process (A), first, the semiconductor substrate 1 on which the film to be processed 2 has been formed is prepared. The film to be processed 2 may be a single layer film of a silicon oxide film or the like, or may be a layered film composing a three-dimensional memory cell array such as a NAND-type flash memory or the like. In an example illustrated in FIG. 1A, the film to be processed 2 is a layered film in which nitride films 21 and oxide films 22 are alternately layered.

Here, in the pattern forming method of the embodiment, the semiconductor substrate 1 may, but not essentially, have the film to be processed 2. Further, in the pattern forming method, a substrate of glass, quartz, mica, or the like can be used in place of the semiconductor substrate 1.

This pattern forming material is applied on the film to be processed 2 of the semiconductor substrate 1. In the case of the dry coating method such as vapor deposition, for example, this pattern forming material itself is applied. In the case of the wet coating method such as spin coating or dip coating, the composition of the embodiment is applied. Next, drying for removal of the organic solvent, and heating or light irradiation for crosslinking are performed as necessary to form the organic film 3 on the film to be processed 2.

The drying is performed in the case of the wet coating method. The crosslinking is performed in a case where the polymer Z contained in this pattern forming material is the crosslinkable polymer Z. The crosslinking is realized by bonding crosslinkable functional groups between different polymer chains. When the curing agent or the like is added, such a bond of crosslinkable functional groups is performed through molecules of the curing agent. In crosslinking, heating or light irradiation may be performed in order to promote a reaction.

When the crosslinking is performed by heating, a heating temperature depends on the kinds of the crosslinkable functional group of the crosslinkable monomer unit and the curing agent. The heating temperature is preferably about 120° C. or higher, more preferably 160° C. or higher, and further preferably 200° C. or higher. Note that, as mentioned above, the heating is preferably performed at a temperature at which $R^2$ is not cleaved off from the monomer unit (3) or the monomer unit (4). Besides, the heating is preferably performed at a temperature at which decomposition of a polymer main chain is suppressed.

For example, when the α carbon of $R^2$ in the monomer unit (3) or the monomer unit (4) is the tertiary carbon, the heating temperature is preferably about 250° C. or lower, and more preferably 200° C. or lower. When the α carbon of $R^2$ is the secondary carbon, the heating temperature is preferably about 300° C. or lower, and more preferably 250° C. or lower. When the α carbon of $R^2$ is the primary carbon, the heating temperature is preferably about 350° C. or lower, and more preferably 300° C. or lower. Note that in the case of the wet coating method, normally, the drying, namely, the removal of the organic solvent contained in the composition of the embodiment is performed collectively by this heating. Thus, the organic film 3 formed of this pattern forming material, or obtained by crosslinking the polymers Z in this pattern forming material can be obtained.

Figure 1B:
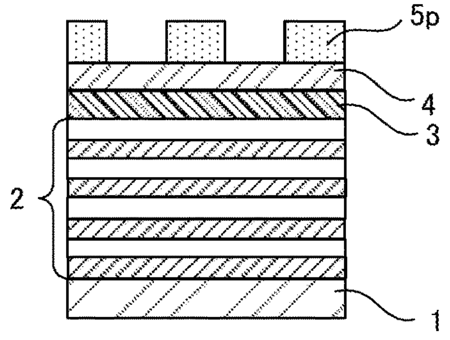
FIG. 1B is a view illustrating one process of the method of manufacturing the semiconductor device according to the embodiment.
Figure 1C:
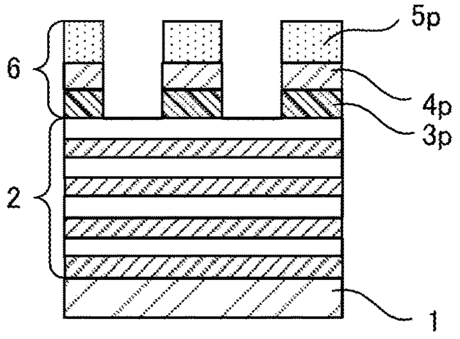
FIG. 1C is a view illustrating one process of the method of manufacturing the semiconductor device according to the embodiment.

FIG. 1B and FIG. 1C are sectional views each schematically illustrating the process (B), namely, the process of patterning the organic film 3 obtained in the process (A). The organic film 3 functions as a under layer of a layered mask structure 6 as illustrated in FIG. 1B and FIG. 1C. FIG. 1B illustrates a state in which a silicon oxide film 4 is formed, on the organic film 3, as a functional film for patterning, and a resist pattern is formed thereon.

The silicon oxide film 4 is formed by, for example, heating a SOG (spin on glass) film formed on the organic film 3 by the following method at a predetermined temperature, for example, 150° C. to 300° C. Note that, similarly to the above, the heating is preferably performed at the temperature at which $R^2$ is not cleaved off from the monomer unit (3) or the monomer unit (4). The SOG film is formed by spin-coating of a wet coating solution in which components of the SOG film is dissolved in an organic solvent, on the organic film 3.

In this event, a not-illustrated antireflection film may be formed on the silicon oxide film 4. The antireflection film allows precision exposure by preventing reflection from a base when a resist film which is formed by the following treatment is patterned. A material such as a novolac resin, a phenol resin, or polyhydroxystyrene can be used as the antireflection film.

Next, the resist film is formed on the silicon oxide film 4, and the resist film is formed into the resist pattern 5*p* by using a lithography technology, an imprint technology, or the like. In the imprint technology, the resist pattern 5*p* is formed by dropping a resist on the silicon oxide film 4, pressing a template in which a fine pattern has been formed against the resist film, and curing the resist film by irradiation with ultraviolet rays.

FIG. 1C is a sectional view illustrating a state after etch-processing the silicon oxide film 4 while using the resist pattern 5*p* as a mask to form a silicon oxide film pattern 4*p*, and further etch-processing the organic film 3 while using the resist pattern 5*p* and the silicon oxide film pattern 4*p* as masks to form an organic film pattern 3*p*. The etching of the silicon oxide film 4 is performed by using fluorine-based gas (F-based gas), and the etching of the organic film 3 is performed by using oxygen-based gas ($O_2$-based gas). As illustrated in FIG. 1C, a structure in which the organic film pattern 3*p*, the silicon oxide film pattern 4*p*, and the resist pattern 5*p* are layered in this order is one example of the layered mask structure 6.

When the antireflection film is formed on the silicon oxide film 4, the antireflection film is patterned before the etching of the silicon oxide film 4. Note that after the formation of the silicon oxide film pattern 4*p*, a film thickness of the resist pattern may be adjusted so that the resist pattern 5*p* disappears. Further, after the formation of the organic film pattern 3*p*, a film thickness of the silicon oxide film pattern 4*p* may be adjusted so that the silicon oxide film pattern 4*p* disappears.

When the organic film pattern 3*p* is formed using the layered mask structure 6 as presented in this embodiment, the silicon oxide film pattern 4*p* and the resist pattern 5*p* being upper layers of the organic film pattern 3*p* may be removed before the process of infiltrating the patterned organic film (organic film pattern 3*p*) with a metallic compound to form a composite film so as to obtain a mask pattern formed of the composite film, which is the process (C).

Figure 1D:
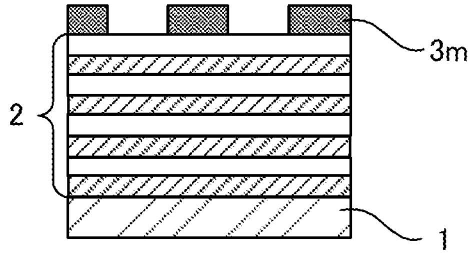
FIG. 1D is a view illustrating one process of the method of manufacturing the semiconductor device according to the embodiment.

FIG. 1D is a sectional view illustrating a state after the process (C), and the organic film pattern 3*p* illustrated in FIG. 1C is metallized to exist as a mask pattern 3*m* on the film to be processed 2 on the semiconductor substrate 1. Note that in the process from the formation of the organic film 3 to the formation of the organic film pattern 3*p*, the condition is adjusted so that $R^2$ at the terminal of the side chain of the monomer unit (3) or the monomer unit (4) derived from the polymer Z is not cleaved off. The metallization of the organic film pattern 3*p* formed in this manner is performed, for example, as follows.

A layered body having the film to be processed 2 and the organic film pattern 3*p* on the semiconductor substrate 1 in this order is carried into a vacuum device, and the organic film pattern 3*p* is exposed to gas or liquid of the metallic compound such as TMA as metal-containing fluid. In this event, molecules of the metallic compound are adsorbed to the carbonyl group of the monomer unit (3) or the monomer unit (4) of the polymer of the organic film pattern 3*p* and $R^2$ is cleaved off as represented in the above reaction formula (F). Then, for example, as represented by the monomer unit (3') in the reaction formula (F), a structure in which the metallic compound ($Al(CH_3)_x$) is firmly bonded to two oxygen atoms of the organic film is formed.

In order to firmly bond the metallic compound to the organic film pattern 3*p* as explained above, the exposure treatment of the metallic compound to the organic film pattern 3*p* is preferably performed under heating. A heating temperature is appropriately selected according to a kind of the metallic compound and a kind of the monomer unit (3) or the monomer unit (4), particularly, a kind of $R^2$. For example, when the metallic compound is TMA and the α carbon of $R^2$ of the monomer unit (3) or the monomer unit (4) is the tertiary carbon, setting the heating temperature at 50° C. or higher, preferably 100° C. or higher makes $R^2$ likely to be cleaved and allows TMA to firmly bond to the organic film.

When the metallic compound is TMA, and the α carbon of $R^2$ of the monomer unit (3) or the monomer unit (4) is the secondary carbon, setting the heating temperature at or higher, preferably 100° C. or higher makes $R^2$ likely to be cleaved and allows TMA to firmly bond to the organic film. Moreover, when the metallic compound is TMA, and the α carbon of $R^2$ of the monomer unit (3) or the monomer unit (4) is the primary carbon, setting the heating temperature at 100° C. or higher, preferably 120° C. or higher makes $R^2$ likely to be cleaved and allows TMA to firmly bond to the organic film. An upper limit of the heating temperature in this case is preferably set to 400° C. in terms of, for example, preventing a main chain of the polymer of the organic film pattern 3*p* from being decomposed.

A metallic compound that is used in a CVD method or an atomic layer deposition (ALD) method can be used as the metallic compound without any particular limitation.

Examples of metals contained in the metallic compound include aluminum, titanium, tungsten, vanadium, hafnium, zirconium, tantalum, molybdenum, and the like.

Among these organometallic compounds and halides, ones having a sufficiently small ligand are usable as the metallic compound.

Concretely, the usable metallic compound can include at least any one of $AlCl_3$, $TiCl_4$, $WCl_6$, $VCl_4$, $HfCl_4$, $ZrCl_4$, TMA, and the like. TMA is preferred in this embodiment.

According to the above, the polymer constituting the organic film pattern 3*p* is metallized to form the mask pattern 3*m* formed of the composite film of the organic film and the metallic compound. Note that after bonding the metallic compound in the organic film pattern 3*p*, the resultant may be subjected to an oxidation treatment such as exposure in a water vapor atmosphere. For example, when TMA is used as the metallic compound in the above, TMA becomes aluminum hydroxide or the like by the oxidation treatment. The oxidation treatment is performed normally using an oxidant such as water, ozone, or oxygen plasma. Note that the oxidation treatment is sometimes performed naturally by moisture in an atmosphere without any special operation.

Figure 1E:
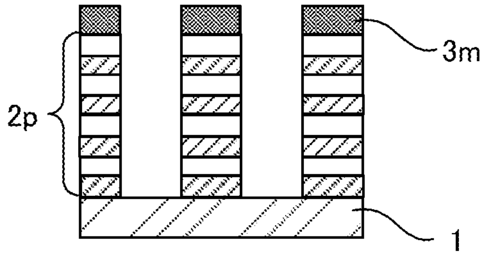
FIG. 1E is a view illustrating one process of the method of manufacturing the semiconductor device according to the embodiment.

Next, the film to be processed 2 is etch-processed by RIE, IBE, or the like by using the mask pattern 3*m* as a mask as illustrated in FIG. 1E, to form into a patterned film to be processed 2*p*. This forms the film to be processed 2*p* provided with a processing shape having a high aspect ratio.

Thereafter, for example, a memory cell array is formed by using an already-known method. For example, it is assumed that a hole pattern is formed in the layered film by the above process. By embedding a block layer, a charge storage layer, a tunnel layer, a channel layer, and a core layer in such a hole, a memory structure can be formed. Thereafter, only nitride films in the layered film are removed through slits formed aside from the hole pattern having the memory structure, and conductive films are alternatively embedded. This causes a layered film in which insulating films (oxide films) and the conductive films are alternately layered. The conductive films in the layered film can be made to function as word lines.

Since this pattern forming material contains the polymer including the monomer unit (3) and/or the monomer unit (4), the metallic compound can be firmly bonded to the organic film obtained by using this pattern forming material owing to the metallization. Then, the composite film obtained by the metallization has high etch resistance and particularly high IBE resistance. This makes it possible to obtain the mask pattern 3*m* with high etch resistance and makes it possible to impart a processing shape having a high aspect ratio to the film to be processed by using this pattern forming material.

When the polymer contained in this pattern forming material is the crosslinkable polymer including the crosslinkable monomer unit having a crosslinkable functional group at a terminal of a side chain in addition to the monomer unit (3) and/or the monomer unit (4), crosslinking the polymers to each other in forming the organic film can make the obtained organic film difficult to be re-dissolved in the organic solvent. This allows an alternative layer film such as the functional film or a precursor film thereof to be formed on the organic film by applying or dropping the wet coating solution or the like. In this event, it is possible to suppress mixing of the organic film with the upper layer film or the precursor film thereof. Examples of the upper layer film or the precursor film thereof include an SOC (spin on carbon) film, a TEOS (tetraethyl orthosilicate) film, a resist film, and the like in addition to the above SOG film, which drastically increases the degree of freedom of design of the layered mask structure.

According to this pattern forming material, the organic film can be formed by the method such as spin coating, dip coating, or vapor deposition. For example, though a carbon deposition layer obtained by using the conventionally used CVD method requires a long time for film formation, the organic film which becomes the composite film having high etch resistance can be formed simply in a short time according to this pattern forming material. The method in which the organic film is formed into the composite film by the metallization is also a simple and economical method. Note that in the case of the wet coating method such as spin coating or dip coating, the composition of the embodiment can be used.

Note that in the above embodiment, the example of metallizing the organic film pattern 3*p* mainly in a gas phase is given, but not limited thereto. The organic film pattern 3*p* may be metallized in a liquid phase.

Further, in the above embodiment, mainly, the structure having the organic film 3, the silicon oxide film 4, and the resist pattern 5*p* is presented as the layered mask structure, but not limited thereto. Various configurations can be employed as the layered mask structure, by inserting various films in addition to the above ones or reducing some of the above films.

In the above embodiment, the mask pattern 3*m* is formed on the semiconductor substrate 1, but not limited thereto. The mask pattern can be formed on a substrate of glass, quartz, mica, or the like in addition to the semiconductor substrate of silicon or the like.

EXAMPLES

The present invention will be explained in more detail by using examples below, but the present invention is not limited to these examples.

Example 1

(2,5-dimethyl-1,3-dicarboxylic acid)benzene was prepared as a starting material and, under reflux, the dicarboxylic acid was made to react with thionyl chloride, and then methanol was made to react in the presence of triethylamine to protect the carboxyl group. Thereafter, a methyl group was brominated by N-bromosuccinimide (NB S) to obtain (2-methyl-5-bromomethyl-1,3-dialkylcarboxylic acid ester) benzene. This was made to react by triphenylphosphine, and then a vinyl group was formed by formaldehyde in the presence of sodium hydroxide. At the same time, deprotection of the dicarboxylic acid protected by the methyl group was proceeded to obtain (2-methyl-5-vinyl-1,3-dicarboxylic acid)benzene.

In DMF (N,N-dimethyl formaldehyde), the obtained (2-methyl-5-vinyl-1,3-dicarboxylic acid)benzene was made to coexist with N,N'-carbonyldiimidazole in a small excess, alcohol ($R^2$—OH) was made to react at room temperature in the presence of 1,8-diazabicyclo[5.4.0]-7-undecen (DBU) to obtain 2-methyl-5-vinyl-1,3-benzene dicarboxylic acid dialkyl ester having a styrene structure.

Note that ethanol was used as $R^2$—OH to obtain a compound 1a-1, isopropyl alcohol was used as $R^2$—OH to obtain a compound 1a-2, and s-butyl alcohol was used as $R^2$—OH to obtain a compound 1a-3.

Besides, (2-t-butyl-5-methyl-1,3-dicarboxylic acid)benzene was prepared as a starting material and subjected to the same reaction as above to obtain compounds 1a-4 to 1a-6.

The obtained compounds 1a-1 to 1a-6 are compounds represented by the general formula (1a) and their substituents are collectively listed in Table 1. In Table 1, H denotes a hydrogen atom, Me denotes a methyl group, Et denotes an ethyl group, i-Pr denotes an isopropyl group, s-Bu denotes an s-butyl group, and t-Bu denotes a t-butyl group.

TABLE 1

| | Substituent | | | |
|---|---|---|---|---|
| Compound | $R^1$ | X | Y | $R^2$ |
| 1a-1 | H | Me | H | Et |
| 1a-2 | H | Me | H | i-Pr |
| 1a-3 | H | Me | H | s-Bu |
| 1a-4 | H | t-Bu | H | Et |
| 1a-5 | H | t-Bu | H | i-Pr |
| 1a-6 | H | t-Bu | H | s-Bu |

10 mmol of each of the obtained compounds 1a-1 to 1a-6 and 0.1 mml of azobisisobutyronitrile (AIBN) as a polymerization initiator were put in a round-bottomed flask, and approximately 5 mL of toluene was added as a polymerization solvent. After the air in the flask was substituted by nitrogen, polymerization was carried out at 100° C. for 8 hours. After the reaction was completed, the flask was made open to the atmosphere to terminate the polymerization, and then a reaction solution was dropped in a large excess of methanol to purify a polymer component by reprecipitation. The obtained solid was filtered off, and the solid was dried in a vacuum to obtain each of desired polymers 1a-1 to 1a-6.

Here, the polymer 1a-1 is a polymer composed of only the monomer unit derived from the compound 1a-1, and the other polymers are also polymers each composed of only the monomer unit derived from the compound having the same code.

Example 2

2-methyl-5-bromomethyl-1,3-benzene dicarboxylic acid dialkyl ester obtained at the middle of the synthesis in the above Example 1 was dissolved into a mixed solvent of acetone and water and made to interact with an ion-exchange resin to obtain 2-methyl-5-hydroxymethyl-1,3-benzenedicarboxylic acid. In DMF, N,N'-carbonyldiimidazole was made to coexist in a small excess, alcohol ($R^2$—OH) was made to react at room temperature in the presence of DBU to obtain 2-methyl-5-hydroxymethyl-1,3-benzene dicarboxylic acid dialkyl ester.

The methacrylic acid chloride was made to react on the obtained 2-methyl-5-hydroxymethyl-1,3-benzene dicarboxylic acid dialkyl ester in the presence of trimethylamine to obtain a desired methacrylate monomer.

Note that ethanol was used as $R^2$—OH to obtain a compound 1b-1, isopropyl alcohol was used as $R^2$—OH to obtain a compound 1b-2, and s-butyl alcohol was used as $R^2$—OH to obtain a compound 1b-3.

Methacrylic acid chloride, which was made to react at the final stage was changed to acrylic acid chloride to obtain acrylate monomers (compounds 1b-4 to 1b-6).

Besides, (2-t-butyl-5-bromomethyl-1,3-dicarboxylic acid ester)benzene obtained at the middle of the synthesis in the above Example 1 was used and subjected to the same reaction as above to obtain compounds 1b-7 to 1b-12.

Besides, (2,4,5,6-tetramethyl-1,3-dicarboxylic acid)benzene was used as a starting material in the above Example 1 to obtain 5-bromomethyl-2,4,6-trimethyl-1,3-benzenedicarboxylic acid dimethyl ester, which was used and subjected to the same reaction as above to obtain compounds 1b-13 to 1b-18.

The obtained compounds 1b-1 to 1b-18 are compounds represented by the general formula (1b) and their substituents are collectively listed in Table 2. In Table 2, H denotes a hydrogen atom, Me denotes a methyl group, Et denotes an ethyl group, i-Pr denotes an isopropyl group, s-Bu denotes an s-butyl group, and t-Bu denotes a t-butyl group.

TABLE 2

| | Substituent | | | |
|---|---|---|---|---|
| Compound | $R^1$ | X | Y | $R^2$ |
| 1b-1 | Me | Me | H | Et |
| 1b-2 | Me | Me | H | i-Pr |
| 1b-3 | Me | Me | H | s-Bu |
| 1b-4 | H | Me | H | Et |
| 1b-5 | H | Me | H | i-Pr |
| 1b-6 | H | Me | H | s-Bu |
| 1b-7 | Me | t-Bu | H | Et |
| 1b-8 | Me | t-Bu | H | i-Pr |
| 1b-9 | Me | t-Bu | H | s-Bu |
| 1b-10 | H | t-Bu | H | Et |
| 1b-11 | H | t-Bu | H | i-Pr |
| 1b-12 | H | t-Bu | H | s-Bu |
| 1b-13 | Me | Me | Me | Et |
| 1b-14 | Me | Me | Me | i-Pr |
| 1b-15 | Me | Me | Me | s-Bu |
| 1b-16 | H | Me | Me | Et |
| 1b-17 | H | Me | Me | i-Pr |
| 1b-18 | H | Me | Me | s-Bu |

10 mmol of each of the obtained compounds 1b-1 to 1b-18 and 0.1 mml of azobisisobutyronitrile (AIBN) as a polymerization initiator were put in a round-bottomed flask, and approximately 5 mL of toluene was added as a polymerization solvent. After the air in the flask was substituted by nitrogen, polymerization was carried out at 100° C. for 8 hours. After the reaction was completed, the flask was made open to the atmosphere to terminate the polymerization, and then a reaction solution was dropped in a large excess of methanol to purify a polymer component by reprecipitation. The obtained solid was filtered off, and the solid was dried in a vacuum to obtain each of desired polymers 1b-1 to 1b-18.

Here, the polymer 1b-1 is a polymer composed of only the monomer unit derived from the compound 1b-1, and the other polymers are also polymers each composed of only the monomer unit derived from the compound having the same code. The example number corresponds to each of the codes.

Example 3

As a comparative example, (5-methyl-1,3-dicarboxylic acid)benzene was used as a starting material to obtain 5-vinyl-1,3-benzenedicarboxylic acid di-s-butyl ester having a styrene structure by the same operation as that in Example 1. Note that in this example, s-butyl alcohol was used as $R^2$—OH. Further, a polymer C1a composed of only the monomer unit derived from the compound was obtained.

Example 4

As a comparative example, 5-bromomethyl-1,3-benzenedicarboxylic acid dialkyl ester obtained at the middle of the synthesis in Example 3 was used and subjected to the same operation as in Example 2 to obtain a methacrylate monomer. Note that s-butyl alcohol was used as $R^2$—OH in this example. Further, a polymer C1b composed of only the monomer unit derived from the compound was obtained.

(Preparation of Pattern Forming Material and Composition for Pattern Formation)

The polymers obtained in the above were made into pattern forming materials without adding a curing agent. PGMEA was added to each of the obtained pattern forming materials so that the content of each of the pattern forming materials was 10 wt %, to prepare each composition for pattern formation.

[Evaluation]

Each of the compositions for pattern formation was used to produce an organic film on a silicon substrate, and the organic film was subjected to a metallization process by the following method to produce a composite film. A metallization property of the organic film and etch resistance of the obtained composite film were evaluated.

(Metallization Property)

A Si substrate subjected to a UV cleaning treatment for 3 minutes in advance was prepared. Each of the compositions for pattern formation was applied onto the Si substrate by spin coating. The number of rotations was adjusted to 2000 to 3500 rpm according to the kind of the polymer, and a solvent was removed by drying after the application, whereby each organic film having a thickness of approximately 300 nm was produced. Further, 200° C. annealing was performed to proceed a crosslinking reaction. The obtained organic film-attached Si substrate was cut into 15 mm square to form a sample for the metallization process.

The metallization was performed by an atomic layer deposition (ALD) film-forming apparatus. Concretely, the metallization was performed in an exposure mode in which a sample for the metallization process was placed in the ALD apparatus, gas-phase TMA was introduced into the apparatus to have a predetermined pressure, and then a valve was closed to keep the pressure in the state for a predetermined time. An initial pressure was set to 900 Pa, and the holding time was set to 600 seconds.

After the exposure to TMA, the gas phase in the apparatus was substituted by water vapor ($H_2O$), the pressure was increased up to a predetermined pressure, and then the valve was closed to keep the pressure in the state for a predetermined time. An initial pressure was set to 300 Pa, and a holding time was set to 200 seconds. The temperature was the same as the temperature at the TMA exposure time. Note that the pressure in the apparatus became gradually lower because $H_2O$ was consumed or adhered to a chamber inner wall. After the holding time under the $H_2O$ filled state elapsed, each metallized sample for the metallization process was taken out of the apparatus. By this operation, TMA was oxidized to form aluminum hydroxide or aluminum oxide.

Here, the ALD apparatus is used for the above metallization process, but the above operation is aimed at impregnation of the polymer with TMA and is not so-called atomic layer deposition (ALD) of depositing an atomic layer on the substrate. Therefore, exposure time to the metallic compound is longer and the number of cycles is smaller than those of normal ALD.

(Etch Resistance)

Each of the metallized organic film-attached substrates (each of the composite film-attached substrates) was subjected to reactive ion etching (RIE) using $O_2$ gas or $CF_4$ gas. Film thicknesses of the composite film of each composite film-attached substrate before and after the RIE were measured by using an atomic force microscope (AFM), and a film thickness difference between before and after the RIE was regarded as an etch amount to calculate an etc rate [nm/sec] per etch time. The results are listed in Table 3 and Table 4. In Table 3 and Table 4, “as spun” represents an etch rate measured under the state before metallization, and “MTLZed” represents an etch rate measured for each metallized organic film.

(1) $O_2$ RIE

The $O_2$ RIE was performed by using CI-300L (manufactured by SAMCO Inc.) under conditions of power: 50 W, bias: 5 W, Flow: 5 sccm, and pressure: 3 Pa.

(2) $CF_4$ RIE

The $CF_4$ RIE was performed by using CI-300L under conditions of power: 50 W, bias: 10 W, Flow: 5 sccm, and pressure: 3 Pa.

The etch resistance for the $O_2$ RIE drastically improves as the degree of metallization increases. The composite film formed of a polymeric material having an ester bond (—C(═O)—O—) on a side chain has high etch resistance against the $O_2$ RIE. It is thought that the metallization was likely to occur and the etch resistance against the $O_2$ RIE increased because there were a lot of carbonyl groups in the component. The etch resistance against the $CF_4$ RIE improves as the degree of metallization increases.

(3) IBE

Ion beam etching (IBE) was performed for each of the organic film-attached substrates (each of the composite film-attached substrates) metallized in the above. Film thicknesses of the composite film of each composite film-attached substrate before and after the IBE were measured by using the atomic force microscope (AFM), and a film thickness difference between before and after the IBE was regarded as an etch amount to calculate an etch rate [nm/sec] per etch time.

(4) RIE Resistance Assuming Memory Holes

Conditions near RIE of memory holes of a three-dimensional memory were assumed, and etching was performed under a mixed gas condition of $C_4F_6$; 80 sccm, Ar; 100 sccm, $O_2$; 54 sccm, and $N_2$; 50 sccm. A film thickness difference between before and after the etching was regarded as an etch amount to calculate an etch rate [nm/sec] per etch time.

TABLE 3

| | $O_2$ RIE rate (nm/s) | | $CF_4$ RIE rate (nm/s) | | Mixed gas RIE rate (nm/s) | | IBE rate (nm/s) | |
|---|---|---|---|---|---|---|---|---|
| Polymer | as spun | MTLZed | as spun | MTLZed | as spun | MTLZed | as spun | MTLZed |
| 1a-2<br>1a-3<br>1a-5<br>1a-6 | 0.3-0.4 | 0.02-0.03 | 0.6-0.7 | 0.2-0.3 | 0.8 | 0.007-0.009 | 0.6 | 0.1-0.2 |
| C1a | 0.3 | 0.02 | 0.6 | 0.2 | 0.8 | 0.01 | 0.6 | 0.3 |

TABLE 4

| | $O_2$ RIE rate (nm/s) | | $CF_4$ RIE rate (nm/s) | | Mixed gas RIE rate (nm/s) | | IBE rate (nm/s) | |
|---|---|---|---|---|---|---|---|---|
| Polymer | as spun | MTLZed | as spun | MTLZed | as spun | MTLZed | as spun | MTLZed |
| 1b-2<br>1b-3<br>1b-5<br>1b-6<br>1b-8<br>1b-9<br>1b-11<br>1b-12<br>1b-14<br>1b-15<br>1b-17<br>1b-18 | 0.4-0.6 | 0.03-0.04 | 0.6-0.7 | 0.4-0.5 | 0.7-0.9 | 0.02-0.03 | 0.7-0.9 | 0.1-0.2 |
| C1b | 0.4 | 0.02 | 0.7 | 0.3 | 0.7 | 0.04 | 0.7 | 0.3 |

As listed in Table 3 and Table 4, it is clear that the composite film formed by using this pattern forming material has high etch resistance. In particular, it was verified that all of the composite films became significantly higher in etch resistance after metallization than those of conventional ones under the etch conditions using the mixed gas near the RIE process for forming the memory holes of the three-dimensional memory.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

<Note>

A polymer containing a monomer unit derived from the compound represented by the general formula (1).

A polymer containing a monomer unit derived from the compound represented by the general formula (2).

A pattern forming method, comprising:

forming an organic film on a substrate by using a pattern forming material; and patterning the organic film and then infiltrating the organic film with a metallic compound to form a composite film and obtain a mask pattern formed of the composite film, wherein the pattern forming material contains a polymer including a monomer unit represented by the following general formula (3) or (4), (3)

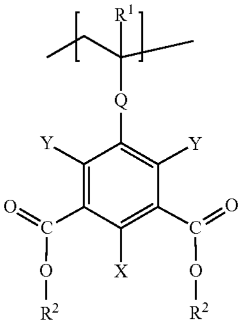

(4)

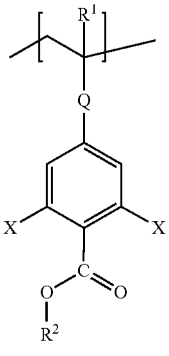

where, in the general formulas (3) and (4), $R^1$ is a hydrogen atom or a methyl group, $R^2$s are independently a $C_{2-14}$ hydrocarbon group in which α carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and X and Y are independently a hydrogen atom or a $C_{1-4}$ hydrocarbon group, at least one of X and Y being the $C_{1-4}$ hydrocarbon group.

The pattern forming method according to the above pattern forming method, wherein in the general formula (3) or (4), $R^2$ is an ethyl group, an n-propyl group, an isopropyl group, an n-butyl group, an isobutyl group, an s-butyl group, or a t-butyl group.

A method of manufacturing a semiconductor device, comprising:

forming an organic film on a film to be processed of a substrate having the film to be processed by using a pattern forming material;

patterning the organic film and then infiltrating the organic film with a metallic compound to form a composite film and obtain a mask pattern formed of the composite film; and processing the film to be processed by using the mask pattern, wherein the pattern forming material contains a polymer including a monomer unit represented by the following general formula (3) or (4).

(3)

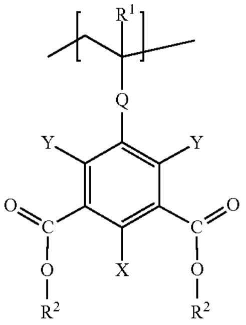

(4)

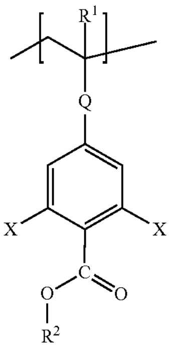

where, in the general formula (3) and (4), $R^1$ is a hydrogen atom or a methyl group, $R^2$s are independently a $C_{2-14}$ hydrocarbon group in which α carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and X and Y are independently a hydrogen atom or a $C_{1-4}$ hydrocarbon group, at least one of X and Y being the $C_{1-4}$ hydrocarbon group.

The method of manufacturing a semiconductor device according to the above method of manufacturing a semiconductor device, wherein in the general formula (3) or (4), $R^2$ is an ethyl group, an n-propyl group, an isopropyl group, an n-butyl group, an isobutyl group, an s-butyl group, or a t-butyl group.

What is claimed is:

1. A polymer including a monomer unit represented by the following general formula (3), (3)

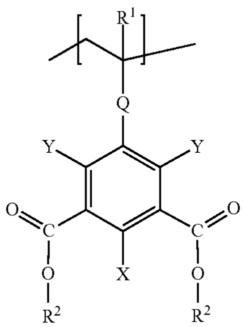

where, in the general formula (3), $R^1$ is a hydrogen atom or a methyl group, $R^2$s are independently a $C_{2-14}$ hydrocarbon group in which a carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and X and Y are independently a hydrogen atom or a $C_{1-4}$ hydrocarbon group, at least one of X and Y being the $C_{1-4}$ hydrocarbon group.

2. The polymer according to claim 1, wherein in the general formula (3), $R^2$s are independently an ethyl group, an n-propyl group, an isopropyl group, an n-butyl group, an isobutyl group, an s-butyl group, or a t-butyl group.

3. The polymer according to claim 1, wherein in the general formula (3), the hydrocarbon groups of X and Y are each a methyl group, an ethyl group, an n-propyl group, an isopropyl group, an n-butyl group, an isobutyl group, an s-butyl group, or a t-butyl group.

4. A polymer including a monomer unit represented by the following general formula (4), (4)

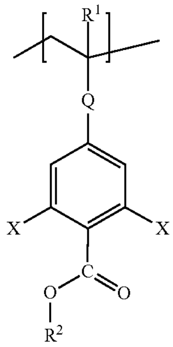

where, in the general formula (4), $R^1$ is a hydrogen atom or a methyl group, $R^2$ is a $C_{2-14}$ hydrocarbon group in which a carbon is a primary carbon, secondary carbon or tertiary carbon, Q is a single bond, a $C_{1-20}$ hydrocarbon group in which the hydrogen atom may be substituted by a halogen atom, or an organic group containing an oxygen atom, a nitrogen atom, or a sulfur atom between carbon-carbon atoms or at a bond terminal of a $C_{1-20}$ hydrocarbon group in which the hydrogen atom may be substituted by a halogen atom, and Xs are independently each an ethyl group, an n-propyl group, an isopropyl group, an n-butyl group, an isobutyl group, an s-butyl group, or a t-butyl group.

* * * * *